United States Patent [19]

Bonutti

[11] Patent Number: 5,454,365

[45] Date of Patent: Oct. 3, 1995

[54] MECHANICALLY EXPANDABLE ARTHROSCOPIC RETRACTORS

[76] Inventor: Peter M. Bonutti, 1303 W. Evergreen Plz., Effingham, Ill. 62401

[21] Appl. No.: 112,884

[22] Filed: Aug. 27, 1993

Related U.S. Application Data

[63] Continuation of Ser. No. 908,848, Jul. 1, 1992, abandoned, which is a continuation of Ser. No. 609,341, Nov. 5, 1990, abandoned.

[51] Int. Cl.⁶ .................................................. A61B 17/02
[52] U.S. Cl. .......................... 600/204; 606/198; 606/192; 606/90; 604/105; 600/207; 600/205
[58] Field of Search .................................. 606/198, 192, 606/63, 90, 200; 604/105–109; 128/20

[56] References Cited

U.S. PATENT DOCUMENTS

| | | | |
|---|---|---|---|
| 832,201 | 10/1906 | Fistler | 606/198 X |
| 1,433,031 | 10/1922 | Pegaitaz | 606/198 |
| 1,863,057 | 6/1932 | Innes | 604/105 |
| 2,854,983 | 10/1958 | Baskin | 604/105 X |
| 3,108,595 | 10/1963 | Overment | 604/105 |
| 3,397,699 | 8/1968 | Kohl | 604/105 |
| 3,517,128 | 6/1970 | Hines | 606/198 |
| 3,557,794 | 1/1971 | Van Patten | 606/198 |
| 3,716,051 | 2/1973 | Fischer . | |
| 3,779,239 | 12/1973 | Fischer et al. . | |
| 3,968,800 | 7/1976 | Vilasi | 606/198 |
| 4,409,974 | 10/1983 | Freedland . | |
| 4,453,539 | 6/1984 | Raftopoulos et al. . | |
| 4,608,965 | 9/1986 | Anspach et al. | 128/4 |
| 4,716,893 | 1/1988 | Fischer et al. . | |
| 4,721,103 | 1/1988 | Freedland . | |
| 4,909,789 | 3/1990 | Taguchi et al. | 606/198 X |
| 4,995,868 | 2/1991 | Brazier | 604/104 X |
| 5,002,557 | 3/1991 | Hasson | 606/191 |
| 5,053,009 | 10/1991 | Herzberg | 604/105 X |
| 5,122,122 | 6/1992 | Allgood | 604/105 X |

FOREIGN PATENT DOCUMENTS

| | | | |
|---|---|---|---|
| 295717 | 12/1899 | France | 606/198 |
| 726041 | 5/1932 | France | 604/108 |
| 2411226 | 9/1974 | Germany | 604/105 |
| 415039 | 5/1947 | Italy | 606/198 |
| 357970 | 11/1972 | U.S.S.R. | 606/198 |
| 214913 | 5/1924 | United Kingdom | 604/106 |

*Primary Examiner*—Michael H. Thaler
*Attorney, Agent, or Firm*—Tarolli, Sundheim & Covell

[57] ABSTRACT

A mechanically expandable retractor for use in arthroscopic surgery. The retractor has an expanding portion at its distal end for expanding against sub-surface tissues when the retractor is in use. The expanding portion includes a plurality of radially expanding The radially outermost surface of each arm when expanded is longitudinally disposed approximately at the distal end of the retractor. The expanding arms can be disposed irregularly circumferentially around the retractor to expand the tissues to provide a working space between adjacent arms. The retractor is inserted through a small percutaneous opening, expanded in sub-surface tissues without significantly damaging the tissue, then collapsed after use for removal. The retractor has a projecting portion at a proximal end of the retractor for manipulating the retractor, to allow the surgeon to push or pull or lever on tissue.

The retractor can be hollow like a cannula to permit the passage of surgical instruments through the retractor, with a side portal into the passage. Alternatively, the retractor can be solid or needle-like. The retractor can include an expandable bladder which can circumscribe the expandable portion of the retractor or be placed elsewhere.

70 Claims, 10 Drawing Sheets

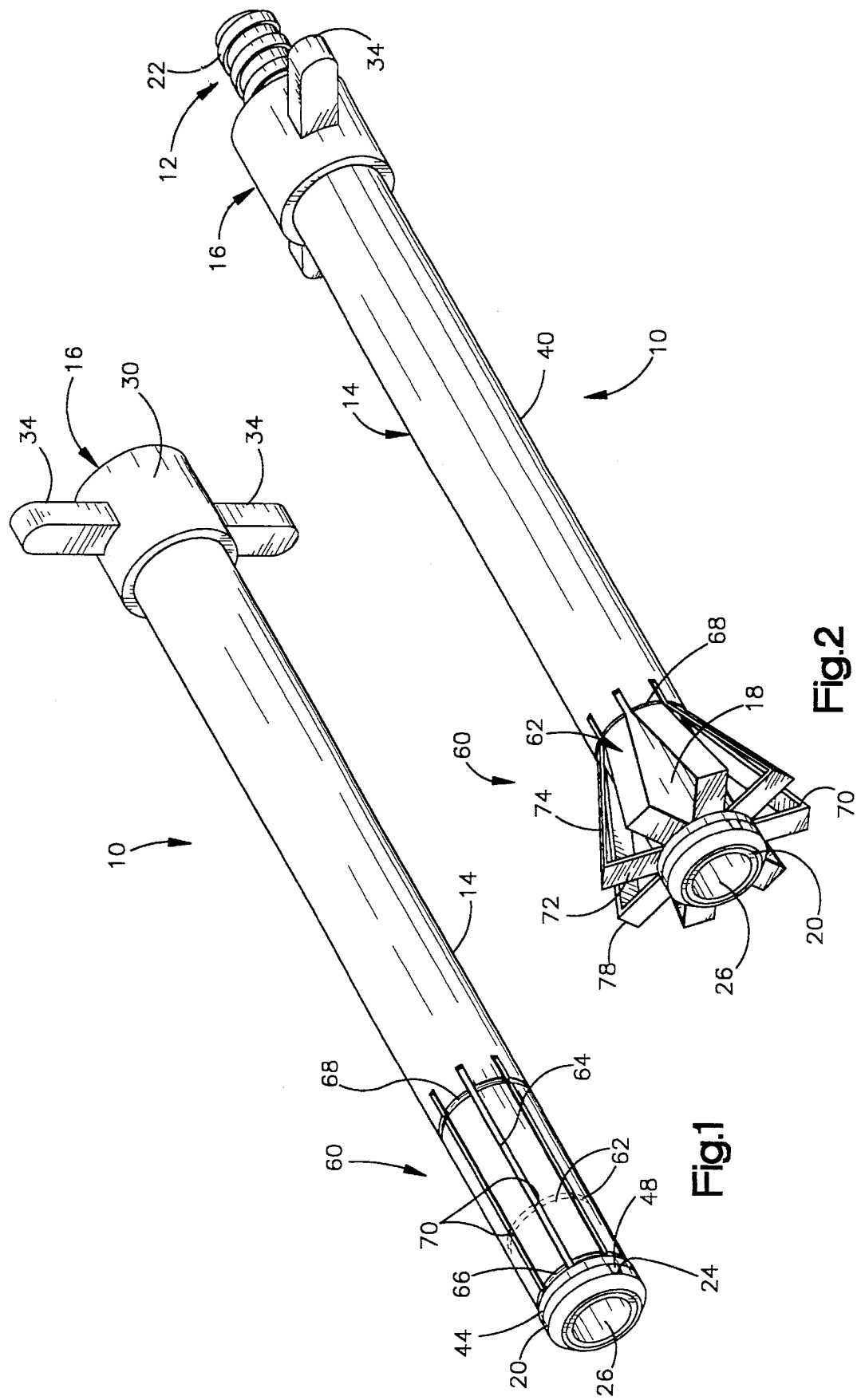

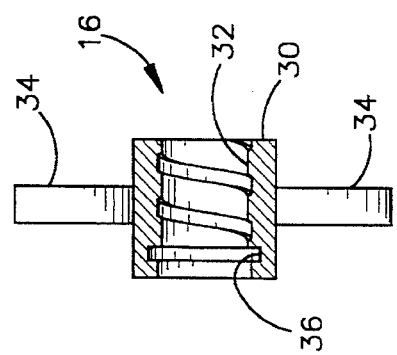
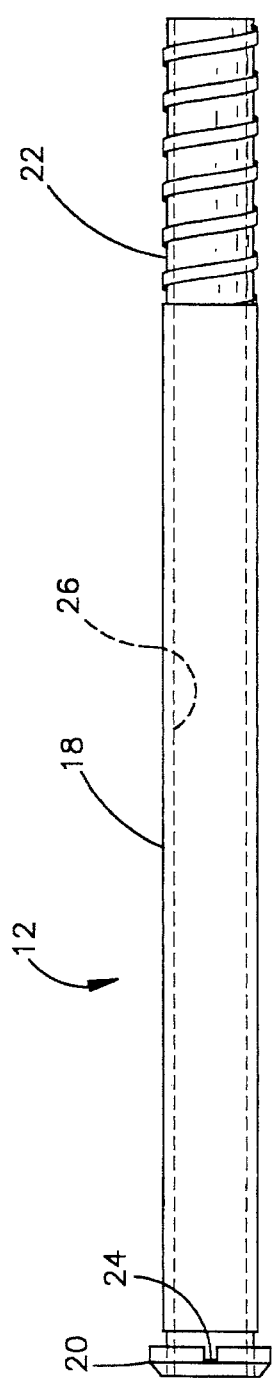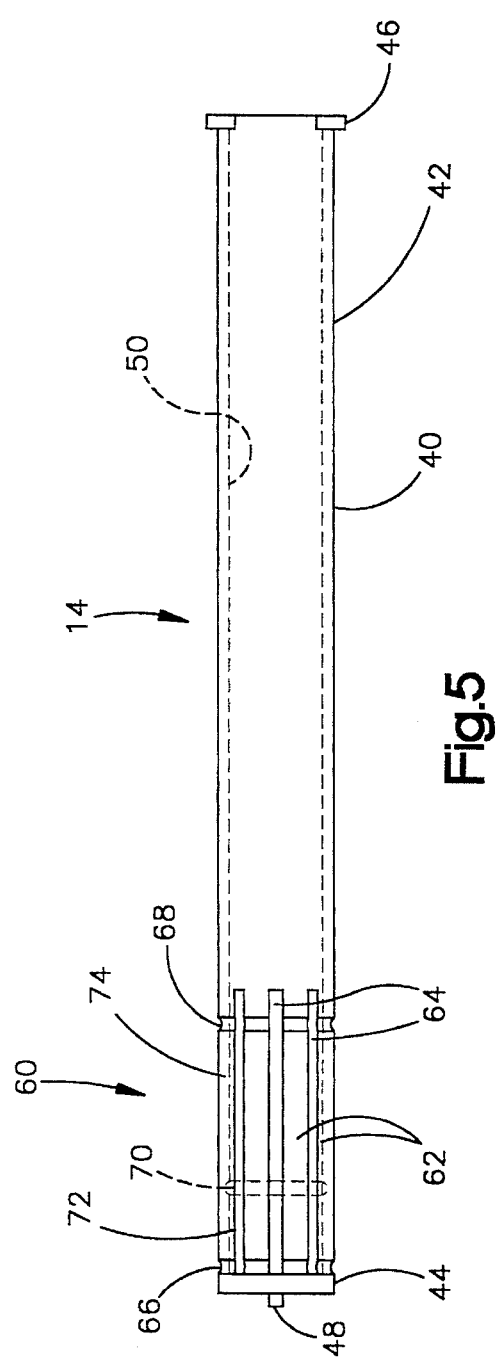

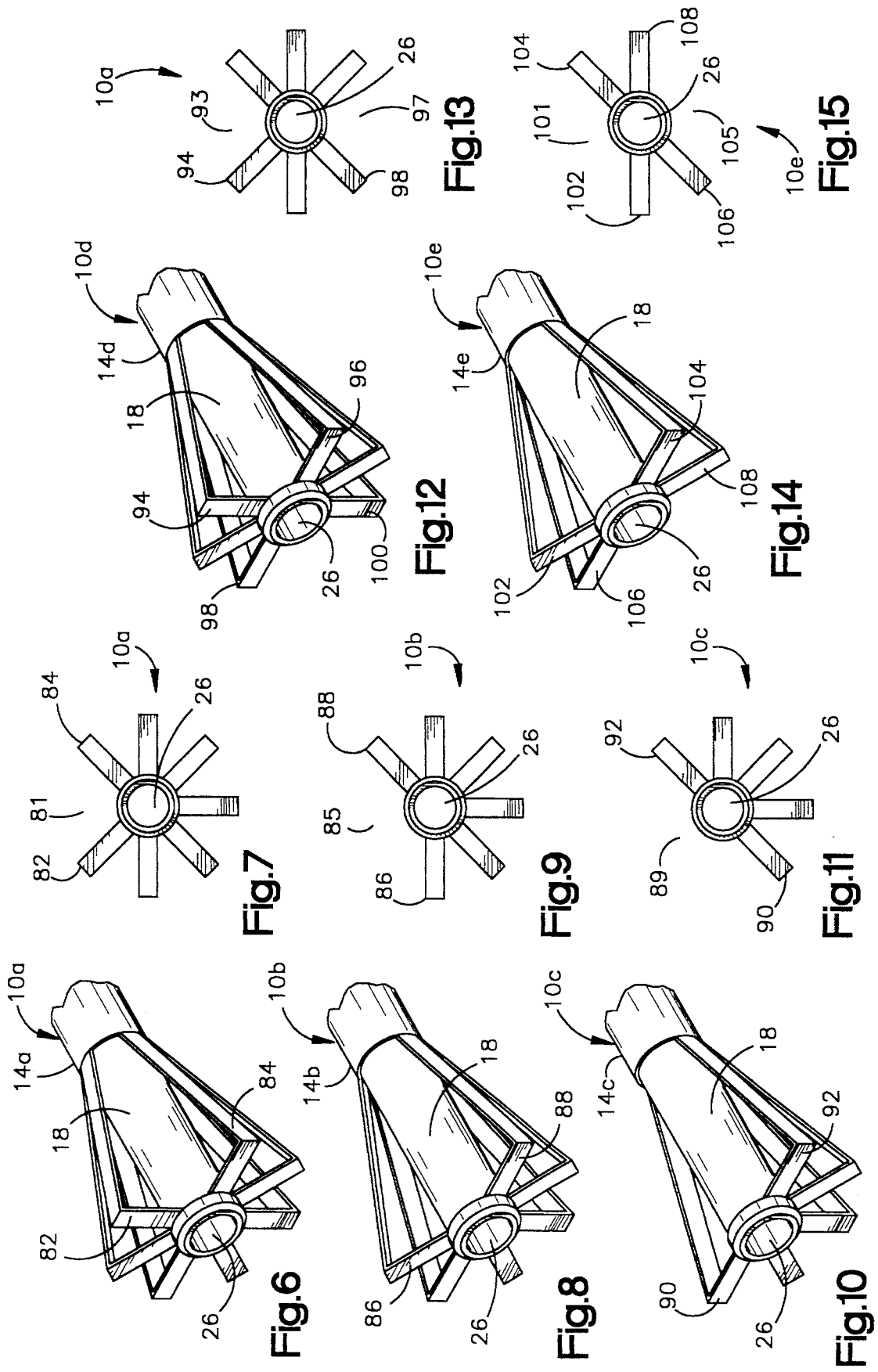

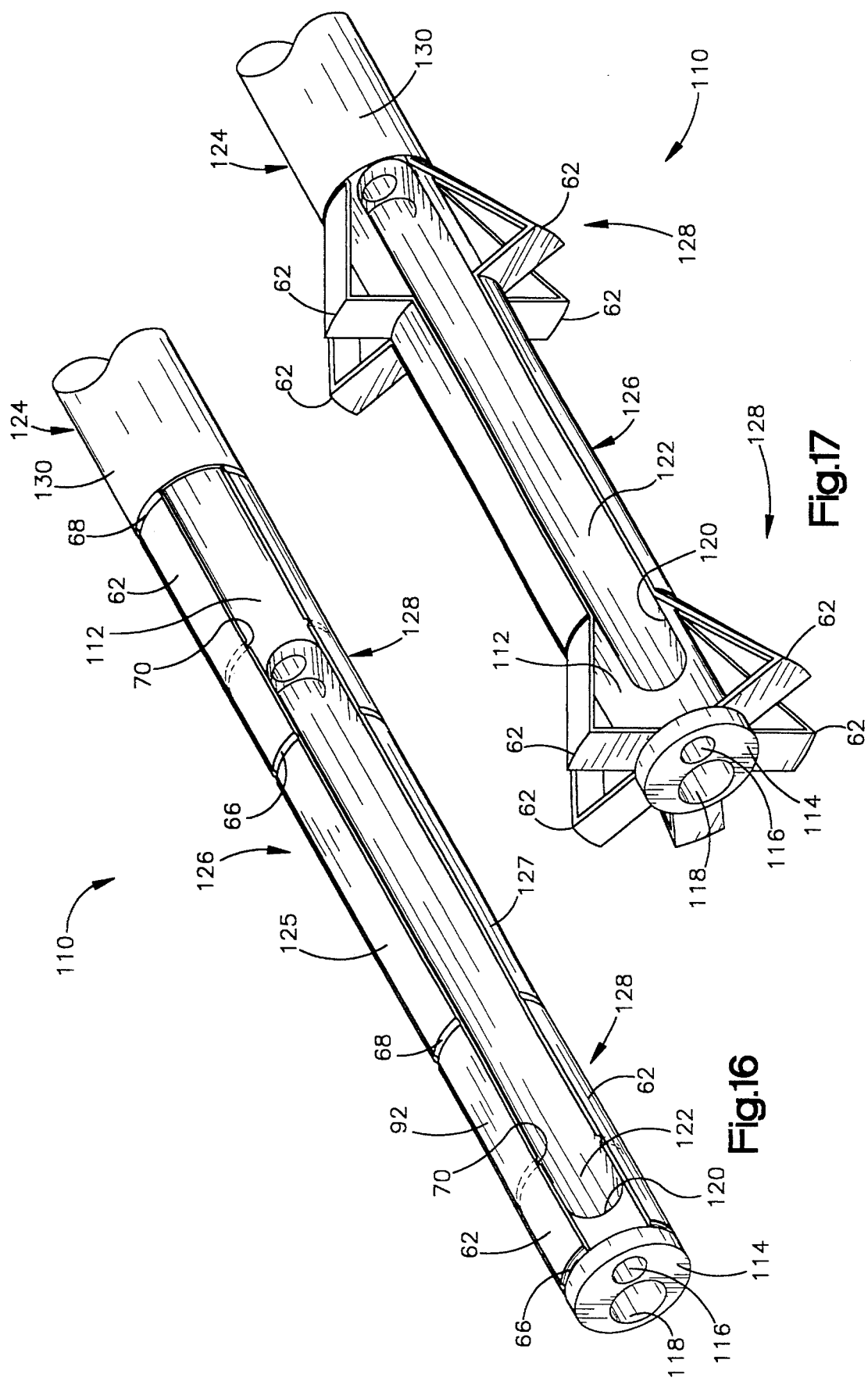

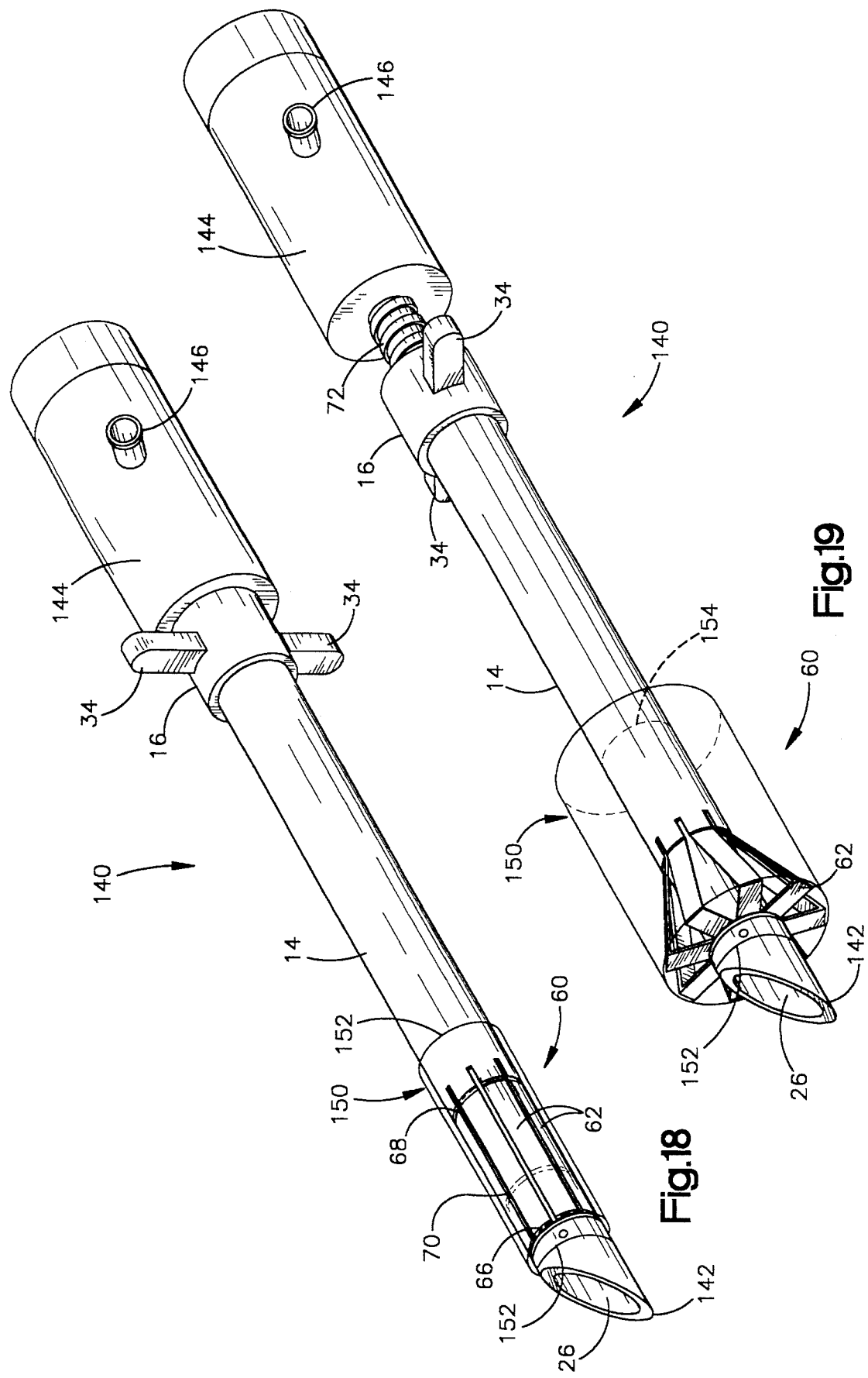

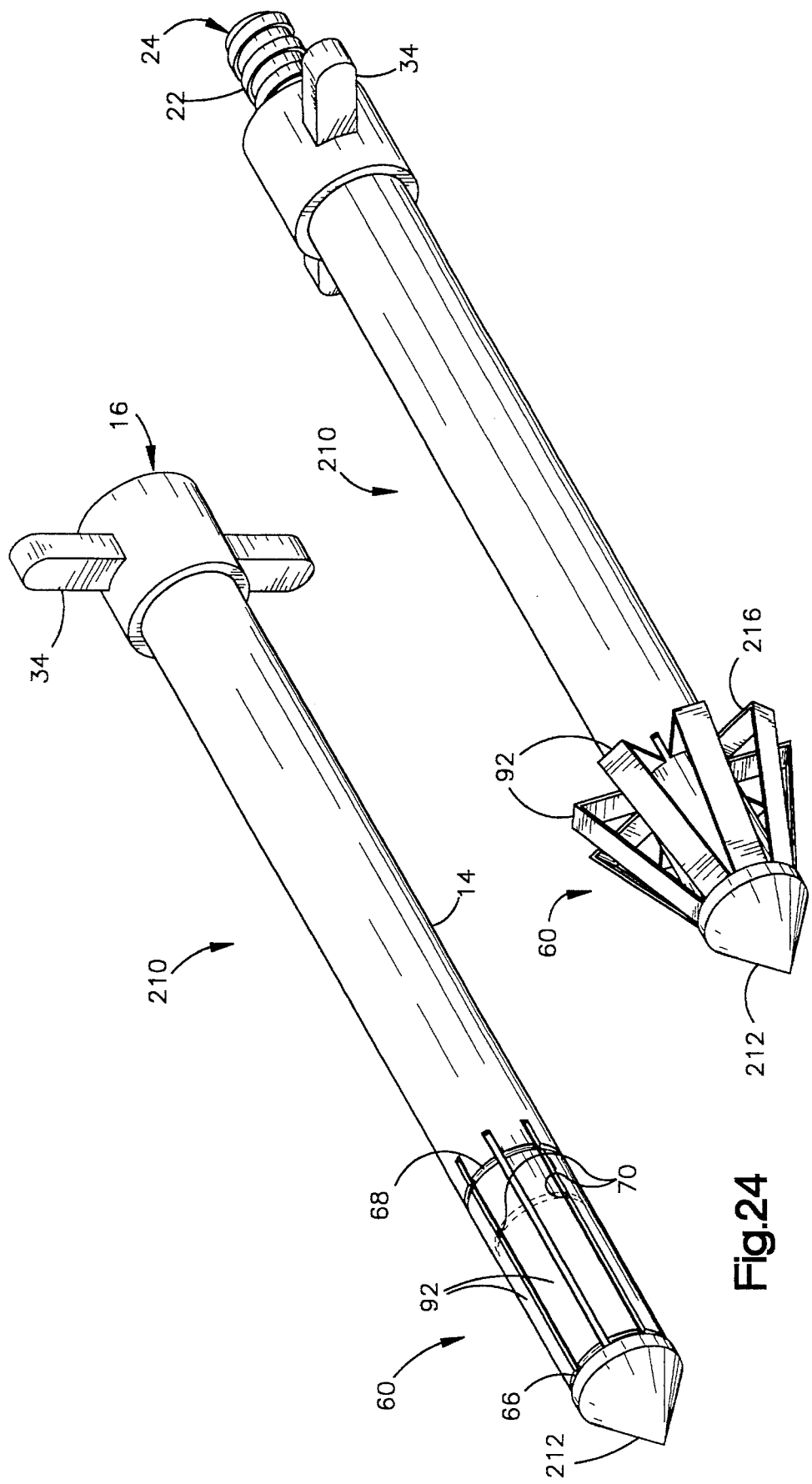

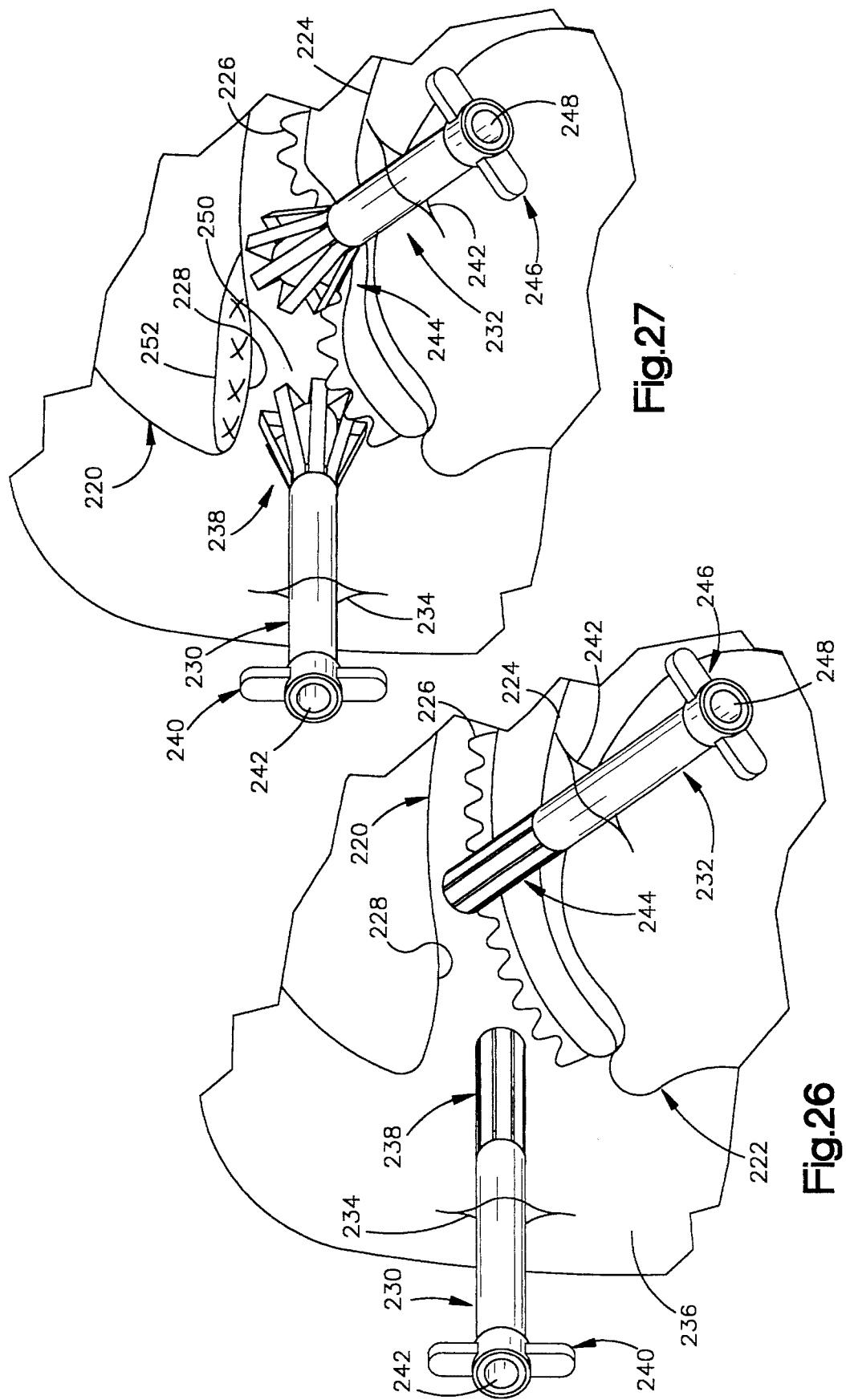

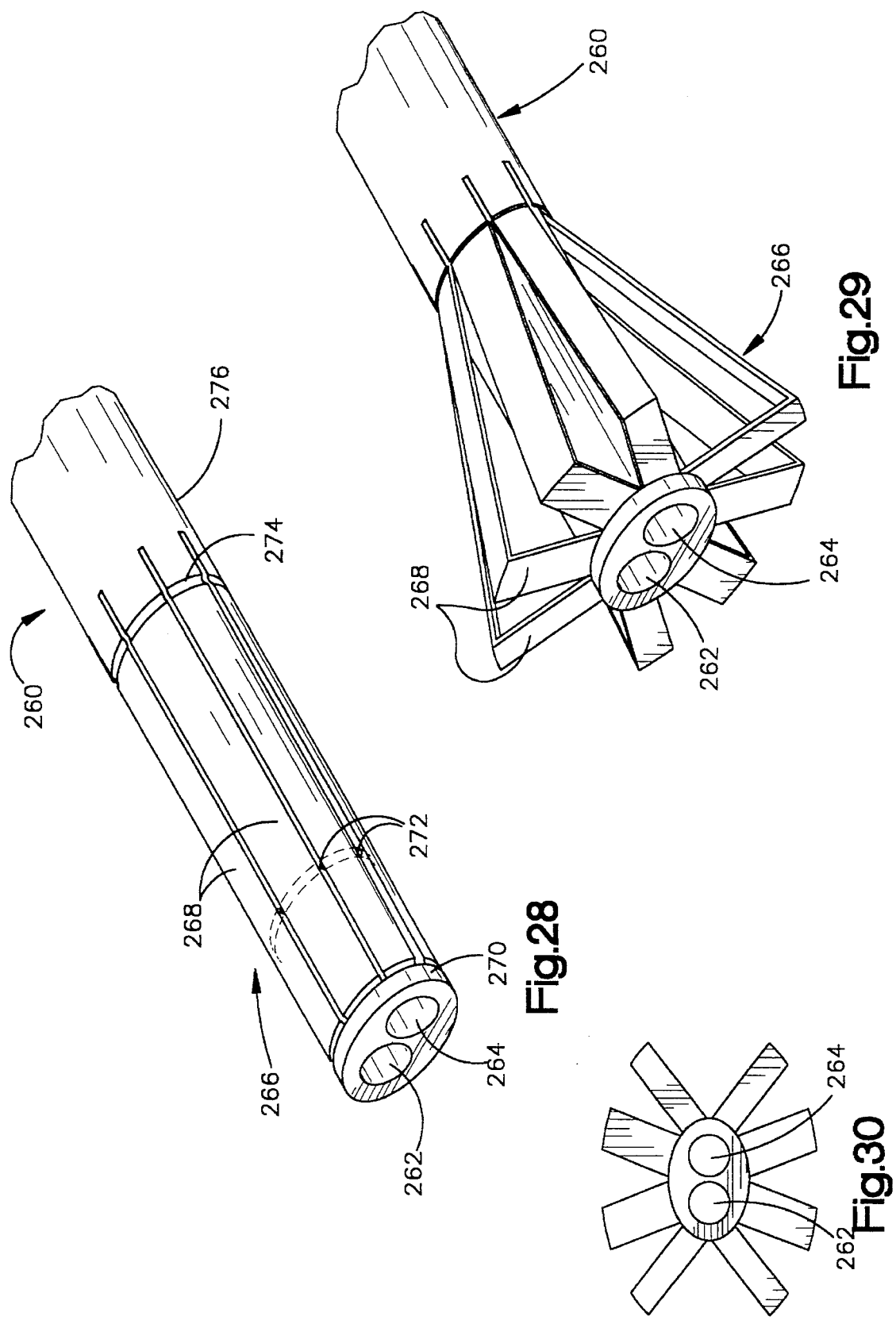

MECHANICALLY EXPANDABLE ARTHROSCOPIC RETRACTORS

This is a continuation of application(s) Ser. No. 07/908,848 filed on Jul. 1, 1992 now abandoned which is a continuation of application Ser. No. 07/609,341 filed on Nov. 5, 1990 now abandoned.

BACKGROUND OF THE INVENTION

The present invention relates to expandable subsurface devices for use in surgery. More particularly, the present invention relates to selectively expandable retractors for use in selectively and specifically moving sub-surface tissue in arthroscopic surgery, endoscopic surgery and fiber optic surgery. (The term "arthroscopic surgery" as used in this application includes endoscopic surgery, fiber optic surgery, and any other type of surgery on sub-surface tissues. Such surgery is performed percutaneously through a small incision or opening in the skin, as opposed to open surgery in which the surgeon cuts through and opens up all superior tissue until all the operating area is exposed.)

Arthroscopic surgery is currently performed without suitable tools for specifically moving tissue and creating visualization and working spaces. Generalized expansion is obtained with $CO_2$, $H_2O$, etc. However, this technique leaves fluid everywhere and is not useful to specifically move tissue.

There are no devices available which allow a surgeon to selectively position various tissue masses encountered during arthroscopic surgery. Delicate tissue such as nerve tissue or blood vessels is put at risk and can be damaged during an operation. Furthermore, the limited space available for the surgeon to work in could make an operation more difficult than it could be.

Retractors designed for use in open surgery are unusable in arthroscopic surgery. Current bladder devices such as a Foley catheter or those used in percutaneous transluminal coronary angioplasty are not useful to retract tissue in arthroscopic surgery, because they are made of a soft, pliable, flimsy material; they work with relatively low pressure; and they have smooth walls and a large surface area of contact so as not to damage the delicate tissues. Such bladder devices also inflate into a non-specific shape, assuming the shape of whatever surface or object they encounter. They do not expand or retract at or near the tip, are not rigid enough to be insertable within a joint or among muscles, tendons and bones, and are too flexible to permit specific tissue retraction. Bladders can also be perforated during surgery.

Such bladder devices also do not provide enough force to move tissue as needed in arthroscopic surgery, mainly because they are designed to dilate an existing stretchable space within the body, such as a blood vessel, and not to create an actual space from a potential space such as in the subacromial bursa or carpal tunnel. In contrast, a great deal more force is needed to selectively move tissues such as muscles, bones, and tendons and expand a potential space therein. One must have a strong, sufficiently rigid instrument to do this, and exert much more force and yet protect delicate tissues. One also needs the ability to specifically direct force in specific locations or directions, not merely randomly. A bladder such as a Foley catheter would deform in an uncontrolled fashion, not pushing where it is needed most.

Accordingly, there exists a need for instruments suitable to mechanically specifically move tissue, which are small enough to fit through a small opening in the skin and which expand to create a working and visualization space in sub-surface tissues. Such instruments must be strong enough and precise enough for use in arthroscopic surgery.

SUMMARY OF THE INVENTION

The present invention is a mechanically expandable retractor suitable for arthroscopic surgery. The retractor has a projecting portion at a proximal end of the retractor for manipulating the retractor. The projecting portion projects from the surface of the body tissues when the retractor is in use. The retractor has at least one expanding portion, which is preferably at the distal end of the retractor for expanding against sub-surface tissues when the retractor is in use. The point of maximum expansion of the retractor expanding portion is preferably as near to the tip of the retractor as possible. An intermediate portion extends between the projecting portion and the expanding portion.

In a preferred embodiment the expanding portion includes a plurality of radially expanding arms. The radially outermost surface of each arm when expanded is longitudinally disposed approximately at the distal end of the retractor. The expanding arms can be disposed irregularly circumferentially around the retractor to provide an eccentric working or visualization space between adjacent arms. The working or visualization space can be 360° around or a lesser portion thereof.

In one embodiment the retractor includes a retractor sleeve and a retractor body, the expanding arms being formed as part of the retractor sleeve which circumscribes the retractor body. The retractor body has a proximal end portion for receiving an expanding force. Axial movement of the body proximal end portion relative to the body distal end portion causes the sleeve to shorten to cause the expanding arms to expand radially outwardly.

The retractor may have a rigid shaft. This allows the surgeon to apply force to sub-surface tissues by pulling or levering or pushing on the projecting portion of the retractor, or by using it as a lever. Alternatively, the retractor may have a flexible shaft, in which case the surgeon can pull on the projecting portion of the retractor to apply force to the sub-surface tissues.

The retractor can include an expandable bladder. The bladder can circumscribe the expandable portion of the retractor, or it can be placed elsewhere along the length or at the tip of the retractor. The bladder can expand either independently of or in conjunction with the expandable portion of the retractor. There can be a plurality of bladders at one axial location. The bladder can be made of a fluid-tight material. Alternatively, the bladder can be made of a perforate material, functioning as a screen. The provision of the bladders with the mechanical expanding portions allows for variable control of the retractor as the surgeon desires.

The retractor can also function as a cannula with an expanding tip. That is, the retractor can have one or more central passages extending longitudinally through at least a portion of the retractor to permit the passage of surgical instruments or a fiber optic scope through the retractor. In this case, it can have a side portal communicating with the central passage and through which surgical instruments or an arthroscope can be passed. The retractor can have two separate passages, one for tools and one for an arthroscope, thus functioning as a dual-lumen cannula. Alternatively, the retractor can be solid or needle-like with or without a removable trocar.

3

The retractor is contracted after use and removed from the body tissues without having significantly damaged the tissues.

The retractor provides the surgeon with the ability to selectively move or retract tissue and to expand a specific space, and to gain a visualization and working space, a function which is not available in present operating instruments.

BRIEF DESCRIPTION OF THE DRAWINGS

Further features of the present invention will become apparent to those skilled in the art to which the present invention relates from reading the following specification with reference to the accompanying drawings, in which:

FIG. 1 is a view of a cannula type retractor in accordance with the present invention, having a plurality of expanding arms, shown in an unexpanded condition;

FIG. 2 illustrates the retractor of FIG. 1 in an expanded condition;

FIG. 3 is a side elevational view of the body of the retractor of FIG. 1;

FIG. 4 is a longitudinal sectional view of the nut of the retractor of FIG. 1;

FIG. 5 is a side elevational view of the sleeve of the retractor of FIG. 1;

FIG. 6 is a pictorial illustration of a retractor having a working space between arms of the retractor;

FIG. 7 is an end view of the retractor of FIG. 6;

FIG. 8 is a pictorial illustration of a retractor having a relatively large working space between arms of the retractor;

FIG. 9 is an end view of the retractor of FIG. 8;

FIG. 10 is a pictorial illustration of a retractor having a larger working space between arms of the retractor then the retractors of FIGS. 6 and 8;

FIG. 11 is an end view of the retractor of FIG. 10;

FIG. 12 is a pictorial illustration of a retractor having a pair of working spaces between arms of the retractor;

FIG. 13 is an end view of the retractor of FIG. 12;

FIG. 14 is a pictorial illustration of a retractor having a pair of relatively large working spaces between arms of the retractor;

FIG. 15 is an end view of the retractor of FIG. 14.

FIG. 16 is a view of a retractor having two axially spaced expanding portions, shown in an unexpanded condition;

FIG. 17 illustrates the retractor of FIG. 16 in an expanded condition;

FIG. 18 is a view of a retractor in accordance with the present invention, and also having an expandable bladder, shown in an unexpanded condition;

FIG. 19 illustrates the retractor of FIG. 18 in an expanded condition;

FIG. 24 is a view of a non-cannula type retractor in accordance with the present invention, shown in an unexpanded condition;

FIG. 25 illustrates the retractor of FIG. 24 in an expanded condition;

FIG. 26 is an illustration of the use of a pair of retractors in arthroscopic shoulder surgery, with the retractors shown in an unexpanded condition;

FIG. 27 is an illustration similar to FIG. 26 with the retractors shown in an expanded condition;

FIG. 28 is a view of an elliptically shaped mechanical retractor, in an unexpanded condition;

FIG. 29 shows the retractor of FIG. 28 in an expanded condition; and

FIG. 30 is an end view of the retractor of FIG. 29.

DESCRIPTION OF PREFERRED EMBODIMENTS OF THE INVENTION

Figure 22:
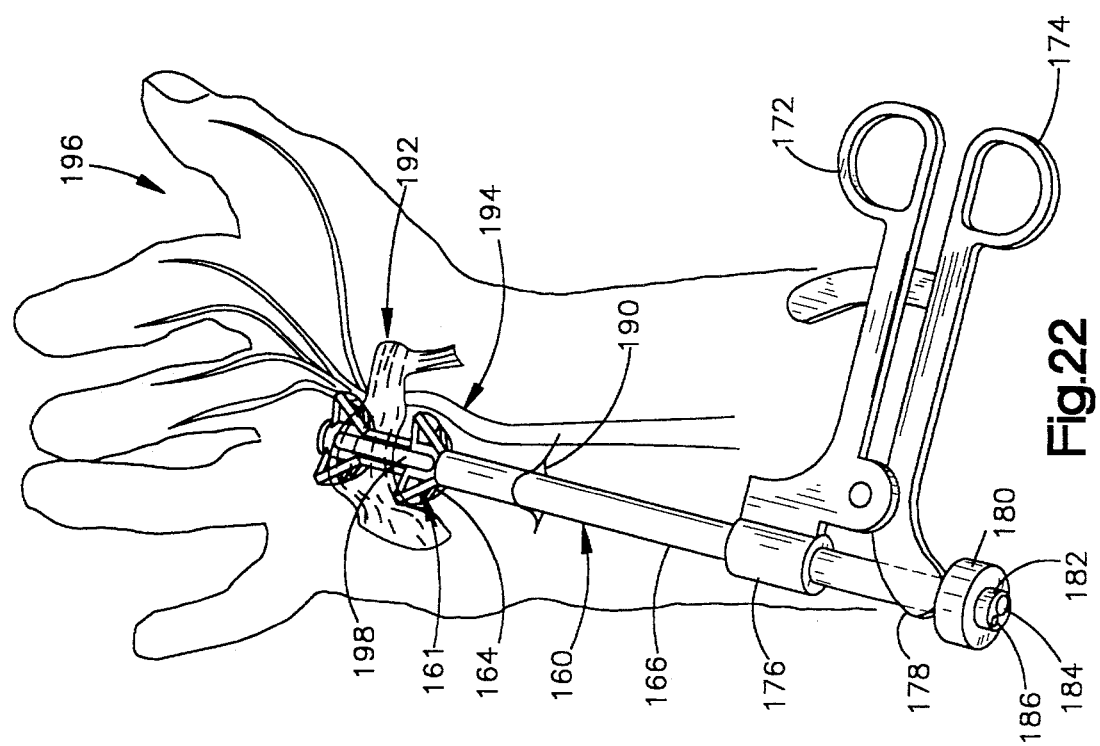
FIG. 22 is a view similar to FIG. 20 with the retractor in an expanded condition.

By way of example, FIGS. 1–5 illustrate an arthroscopic retractor 10 in accordance with the present invention. The retractor 10 includes a retractor body 12, a retractor sleeve 14 and a nut 16.

The hollow tubular retractor body 12 (FIG. 3) includes a central portion 18, a widened distal end portion 20, and a threaded proximal end portion 22. The distal end portion 20 is of a larger diameter than the remainder of the retractor body 12. A pair of diametrically opposed notches 24, only one of which is seen in FIG. 3, are formed in the distal end portion 20. A central passage 26 extends longitudinally the entire length of the retractor body 12. The passage 26 is large enough for arthroscopic surgical instruments to pass through. The central portion 18 is rigid to allow manipulation of the distal end portion by moving the proximal end portion. Alternatively, the central portion could be flexible for easier positioning in the body. The threaded proximal end portion also includes suitable means (not shown) such as a clamp to hook up arthroscopic instruments, or to lock the retractor 10 on to such a device.

The nut 16 (FIG. 4) includes a body portion 30 having a threaded bore 32 for receiving the threaded end portion 22 of the retractor body 12. The nut 14 is enlarged to form a pair of handles 34 which extend from the body portion 30 of the nut 16. The handles 34 can be grasped by a surgeon to rotate the nut 16, and to manipulate the retractor 10 as a whole. An annular slot 36 is formed in the distal end portion of the nut 16.

The hollow tubular retractor sleeve 14 (FIG. 5) includes a central portion 40, a proximal end portion 42, and a distal end portion 44. The proximal end portion 42 has an oblong widened portion 46 which is received in the slot 36 in the nut 16. The distal end portion 44 has a pair of diametrically opposed projections 48, only one of which is shown in FIG. 5. The projections 48 are received in the notches 24 in the distal end portion 20 of the retractor body 12. A central passage 50 extends longitudinally through the entire length of the retractor sleeve 14. The passage 50 is sized to receive the central portion 18 and the proximal end portion 22 of the retractor body 12. The central portion 40 is rigid to allow manipulation of the distal end portion by moving the proximal end portion. Alternatively, the central portion could be flexible for easier positioning in the body.

The retractor sleeve 14 also includes an expanding portion 60. The expanding portion 60 includes a plurality of circumferentially spaced expanding arms 62. Adjacent arms 62 define between them a series of slots 64. The expanding portion 60 illustrated in the embodiment of FIGS. 1–5 has eight equally spaced arms 62 over a 360° range. It should be understood that the present invention contemplates that any different number of arms can be used, and they can be spread equally or unequally over a different circumferential extent, in order to provide varying or eccentric expansion.

Each expanding arm 62 extends between a groove 66 adjacent the distal end portion 44 of the sleeve 14, and a groove 68 adjacent the central portion 40 of the sleeve 14. The grooves 66 and 68 are formed on the exterior of the material of the sleeve. An intermediate groove 70 is formed on the interior of each arm 62 and divides each arm 62 into a distal expanding portion 72 and a proximal expanding portion 74. The grooves 66, 68, and 70 weaken the material of the sleeve 14. When force is directed axially on the distal end portion 44 of the sleeve 14 in a direction toward the proximal end portion, the material of the sleeve 14 buckles at the weakened areas of the grooves 66, 68, and 70, causing the arms 62 to expand radially outwardly.

To assemble the retractor 10, the hollow sleeve 14 is slid axially over the proximal end portion 22 of the body 12. The distal end portion 44 of the sleeve 14 engages the widened distal end portion 20 on the body 12. The projections 48 on the sleeve 14 engage the notches 24 on the body 12, blocking rotation of the sleeve 14 relative to the body 12. (Other structures can be used to obtain this blocking function. For example, if the retractor parts are injection molded, a key and keyway structure may be used for ease of manufacture.) At least a portion of the threaded proximal end portion 22 of the body 12 is exposed. The nut 16 is threaded onto the exposed proximal end portion 22 of the body 12. The widened portion 46 of the sleeve 14 is received in the slot 36 in the nut 16.

To operate the retractor 10, the nut 16 is rotated on the threaded proximal end portion 22 of the body 12, decreasing the distance between the nut 16 and the distal end portion 20 of the body 12. The sleeve 14 is compressed axially. The sleeve 14 buckles at the grooves 66, 68, and 70. The arms 62 on the sleeve 14 move radially outwardly from an unexpanded condition as shown in FIG. 1 to an expanded condition as shown in FIG. 2. (Any system for shortening the sleeve other than a threaded system can be used also.)

The radially outermost surface 78 of each expanded arm 62, which is the radially outermost point of the retractor 10, is located axially at the distal end of the retractor 10. Because the retractor 10 expands at its distal end, not at a mid-portion, stability is increased, since the surgeon is holding the retractor 10 at its proximal end and the retractor 10 is firmly positioned at its distal end. Also, the expanded retractor 10 thus creates a working space where the surgeon needs it, without having to go further down with the instrument as would be necessary if the expanding portion were axially centrally located. The retractor 10 is rigid in a transverse direction, and therefore the surgeon can pull push or lever it to manipulate subcutaneous tissue.

There are a variety of ways in which the expanding portion of a retractor in accordance with the present invention can be configured for particular surgical applications. In the retractors shown in FIG. 6, the expanding arms 62 are disposed irregularly circumferentially around the retractor to provide an increased working space or operating area between particular pairs of expanding arms 62. The external shape of the retractor when expanded, and the amount of expansion, are designed for the specific application on which that retractor is to be used. For example, if the surgeon is working against bone, he can select a retractor which is configured so that it stays flat against the bone, and expands away in the opposite direction, to push tissue away from the bone and create a working and visualization space next to the surface of the bone.

The retractor of the present invention, therefore, is not merely a round structure which expands. It allows mechanical manipulation of tissue, a function which is not available now in arthroscopic surgery. It can be in the shape of an umbrella; oval; wedge; cone; triangular; I-beam; a half-moon shape to protect a nerve; a V-shape to push a nerve in a different direction; a V-shape which expands at the tip; T-shaped or L-shaped; or other shapes as desired.

As an example, the retractor 10*a* (FIGS. 6 and 7) includes a sleeve 14*a* similar to the sleeve 14 of the retractor 10, but with one less expanding arm. An enlarged working space 81 is formed between the arm 82 and the arm 84 of the sleeve 14*a*. A greater portion of the retractor body central portion 18 is thus exposed.

Similarly, the retractor 10*b* includes a sleeve 14*b* having six expanding arms. A larger working space 85 is created between the arms 86 and 88, exposing a larger portion of the body central portion 18. In the retractor (FIGS. 10 and 11), the sleeve 14*c* has only five radially expanding arms, creating a 180° working space 89 between the arms 90 and 92.

In the retractor 10*d* (FIGS. 12 and 13), six expanding arms are spaced circumferentially around the sleeve 14*d* to expose the retractor body central portion 18 on opposite sides. A working space 93 is created between the arms 94 and 96 on one side, and a working space 97 is created between the arms 98 and 100 on the opposite side. In the retractor 10*e* (FIGS. 14 and 15), only four expanding arms are present, and even larger working spaces are created on opposite sides, that is, a space 101 between the arms 102 and 104 on one side, and a space 105 between the arms 106 and 108 on the opposite side.

It can thus be seen that the retractor 10 can be configured to meet almost any application, by appropriately locating and sizing and configuring the expanding portion of the sleeve 14 of the retractor. For example, there may be provided longer expanding arms to provide for a greater amount of expansion. The arms may in such a case may be made thicker for greater strength. All such configurations are included within the scope of the present invention.

Also included are structures functionally equivalent to the expanding arm construct. For example, the expanding portion of a retractor in accordance with the present invention may be as simple as an expansion device like a screw jack or an inflatable bladder disposed between two opposed plates which spread apart upon actuation of the expansion device.

The central passage 26 through the body portion of the retractor 10 effectively allows the retractor 10 to serve as a cannula through which surgical instruments can be passed even when the retractor is in use. If a side portal is provided in the retractor as described below, surgical instruments, tools, fluid lines, etc. can be passed into or out of the retractor through the side portal.

Another important feature of the retractors of the present invention is that they can be contracted after use of the retractor to allow the retractor to be removed from the operating area. The structure of the retractor allows for safe decompression (contraction) and removal of the device after use. For example, in the retractor illustrated in FIGS. 1–5, the widened portion 46 of the retractor sleeve 14 is received in the slot 36 in the nut 14. After expansion of the sleeve as described above, when the nut 14 is rotated back so as to move away from the distal end portion 20 of the retractor body 12, the nut 14 pulls the widened portion 46 of the sleeve 14, lengthening the sleeve and causing the arms 62 to contract to their starting (unexpanded) position. The retractor 10 can then be removed easily from the operating site, without having significantly damaged any tissue. This feature is not available with any previous mechanical expanding devices such as expanding bone screws.

FIGS. 16 and 17 illustrate another embodiment of the invention in which a retractor 110 includes two separate axially spaced expanding portions and also has a side portal through which an arthroscope and/or other arthroscopic surgical instruments may be passed.

The retractor 110 includes a hollow retractor body 112 having a distal end portion 114 with a tool hole 116 and a scope hole 118. An edge 120 defines an opening or side portal 122 in the retractor body 112. The opening 122 communicates with a central passage extending axially through the body 112.

The hollow tubular retractor sleeve 124 includes an intermediate portion 126, a pair of expanding portions 128 on either side of the intermediate portion 126, and a proximal sleeve portion 130. Each expanding portion 128 of the sleeve 124 includes a plurality of arms 62 similar to the expanding arms 62 in the embodiment illustrated in FIGS. 1–5. Each circumferentially aligned pair of arms 62 is connected by an intermediate sleeve segment such as the segments 125 and 127. In the retractor 110, the expanding arms 62 are spaced circumferentially about the sleeve 14 so that the space between the intermediate segments 125 and 127, as well as the space between adjacent arms 62, is aligned with the opening 122 in the retractor body 112.

Accordingly, when the retractor 110 is expanded as illustrated in FIG. 17, there is access from the central passage of the retractor body 112, through the opening 122, and between adjacent intermediate segments and adjacent expanding arms, for the passage of surgical instruments. Furthermore, the pair of expanding portions 128 move tissue out of the way at axially spaced locations along the retractor 110, to provide a large working area extending longitudinally between the two expanding portions 128 of the retractor. In similar fashion, expanding portions like or similar to the expanding portions 128 can be placed at selected locations along a retractor in accordance with the present invention, in order to selectively retract tissue for a particular application. Two or more separate retractors can also be used for this function.

In another embodiment of the invention, an inflatable bladder is included on the mechanically expandable retractor. The bladder can be co-extensive with the expanding portion of the retractor, or it can be spaced apart from the expanding portion of the retractor. The bladder can be used independently or in conjunction with the mechanical retractor.

FIGS. 18 and 19 illustrate an embodiment of the invention which includes an inflatable bladder circumscribing the expanding portion of the retractor. A retractor 140 includes a sleeve 14 with an expanding portion 60 including a plurality of expanding arms 62. The body portion of the retractor 140 has a pointed distal end 142 for easier passage through tissues. Proximal to the threaded portion 22 of the retractor body, a portion 144 of the retractor includes a fluid supply port 146. An inflatable bladder 150 is bonded to the retractor sleeve 14 at two circumferential, axially spaced locations 152 and 154. Appropriate fluid passages are provided in the retractor body and the retractor sleeve to provide fluid communication between the fluid supply port 146 and the bladder 150. The bladder can be deflated with suction.

The bladder 150 inflates and expands radially upon the introduction of fluid under pressure into the fluid supply port 146. The bladder 150 can be inflated independently of expansion of the expanding portion 60 of the retractor 140. Alternatively, the bladder 150 can be expanded in conjunction with expansion of the expanding portion 60 of the retractor 140, in which case it may be preferable to have the bladder in the shape of the mechanical retractor.

The bladder 150 prevents tissue from being caught in between the expanding arms 62 to minimize tissue damage when the retractor is in use and to allow for easy contraction and removal of the retractor after use. The bladder 150 insures proper operation of the expanding portion 60 by keeping tissues out of its way to provide more uniform retraction. The bladder 150 has a tamponade effect, lessening bleeding in the surrounding tissues. The bladder 150 also spreads the retractive force, lessening the risk to delicate tissues such as nerve tissue.

An expandable bladder such as the bladder 150 can be provided at other locations along a retractor 140. For example, a bladder can be provided at a location spaced apart from any expanding portion of the retractor. Also, a bladder can be provided which spans longitudinally the distance between two expanding portions on a retractor. The bladder can be formed of a fluid tight material in order to maintain fluid pressure and exert greater force against the tissues of the body. The bladder can alternatively be made of a perforate material which allows fluid flow therethrough but which also serves to apply force against the tissue it encounters. The bladder may be reinforced, of a dual durometer layered construction, ribbed, or have a specific molded shape. The bladder may be constructed in accordance with co-pending application Ser. No. 487,645, filed on Mar. 2, 1990 now U.S. Pat. No. 5,331,975, the disclosure of which is incorporated by reference.

One basic purpose of the bladder on a retractor of the present invention is to maintain a separation between the expanding arms and the tissues they expand against. Therefore, the bladder need not be made of a fluid-tight material if the bladder per se is not to be expandable. If desired, the bladder can merely be a fabric, mesh, film, polymer, or other material extending over the expanding arms and moving radially outwardly with them. Whether the bladder is fluid-tight or not, the material of the bladder can be bonded directly to the arms. The material can be stretchable to expand when the expanding arms move radially outwardly then contract when the arms move back inwardly.

Use of only a bladder (without a mechanical retraction device) has the disadvantage that a bladder can be punctured with a surgical knife or cutter and will collapse, losing all the retraction gained upon inflation and possibly compromising the surgery. Because the retractors of the present invention are also mechanical in nature, this possibility is avoided, and secure retraction is provided.

Figure 20:
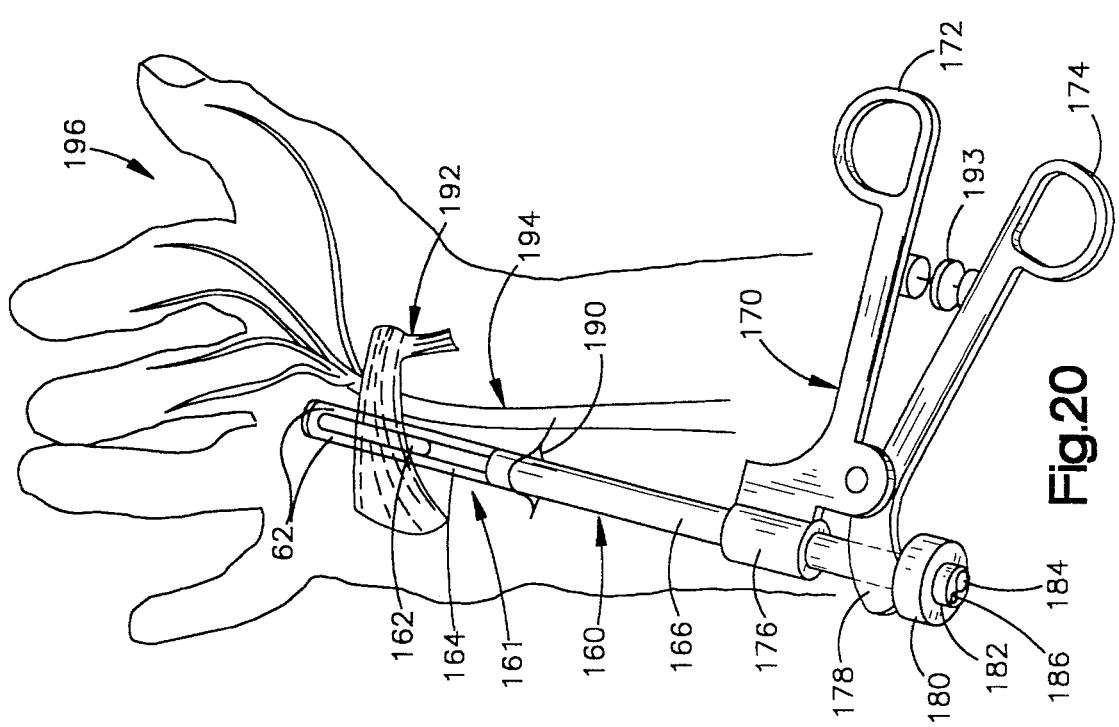
FIG. 20 is a view showing a retractor being used in carpal tunnel surgery, in an unexpanded condition.
Figure 21:
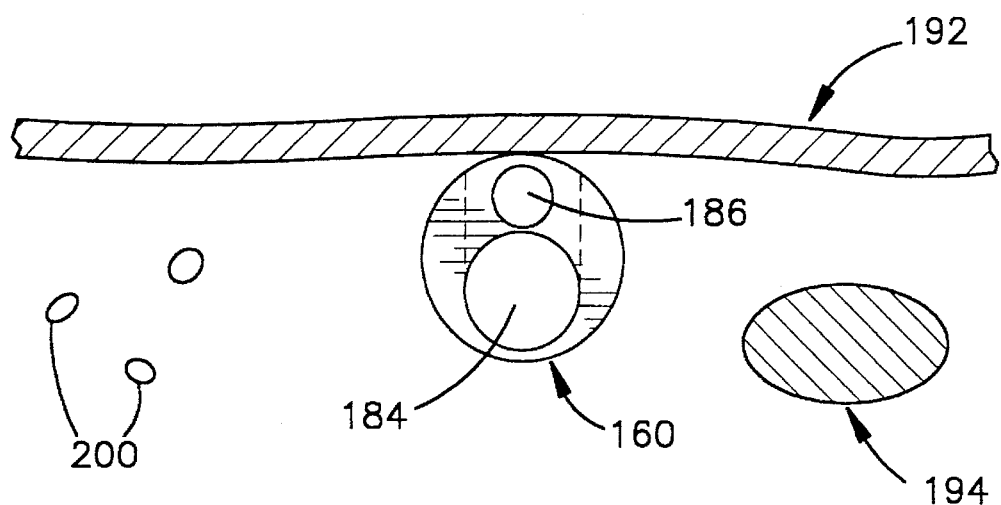
FIG. 21 is a simplified transverse sectional view of the operating area of FIG. 20.

FIGS. 20 through 23 illustrate the use of a retractor in accordance with the present invention in carpal tunnel surgery. The retractor 160 is illustrated in FIGS. 20 and 21 in an unexpanded condition, and in FIGS. 22 and 23 in an expanded condition. The retractor 160 is inserted through an incision 190 in the wrist, and underneath the transverse carpal ligament 192, adjacent the median nerve of a hand 196.

The retractor 160 includes an expanding portion 161 with a plurality of expanding arms 62, two of which are spaced about an opening or side portal 162 for instrument passage therethrough. An expanding bladder 164 is bonded to the sleeve 166 of the retractor 160. The retractor 160 is secured in a holder 170 having a pair of grips 172 and 174. The grip 172 is fixedly attached to a sleeve clamp 176 which securely clamps the sleeve 166 of the retractor 160. The grip 174 is fixedly attached to a portion 178 for engaging a widened portion 180 on the body portion 182 of the retractor 160. The body portion 182 has a scope hole and a tool hole 186 extending therethrough. Suitable locking means can also be provided to lock the retractor in a particular expanded condition.

Figure 23:
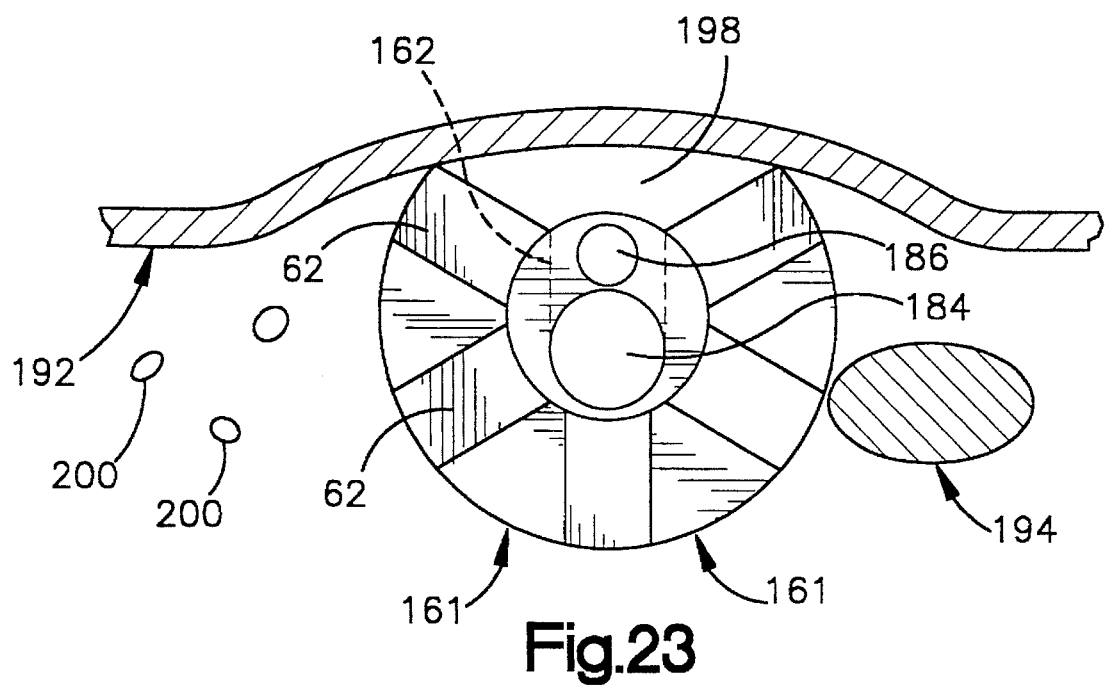
FIG. 23 is a simplified transverse sectional view of the operating area of FIG. 22.

FIGS. 22 and 23 illustrate the retractor 160 in an expanded condition. Relative movement of the grip 172 toward the grip 174 draws the body portion 182 proximally relative to the clamped sleeve portion 166, expanding the expanding portion 161. The expanding arms 62 move radially outwardly to create a working or operating area 198 adjacent the ligament 192. The bladder 164 is also expanded about the expanding portion 60 of the retractor 160. Tissue is not significantly damaged by the retractor 160. After the operation is completed, the retractor 160 is simply contracted or collapsed and removed from the operating site.

Because of the controlled expansion of the retractor 160, the median nerve 194 is shielded from the operating area. Tools and an arthroscope may be passed through the opening 162 into the operating area 198, while the median nerve 194 and other tissues such as tendons 200 are safely shielded from the operating area 198. Accordingly, by use of the retractor 160, the surgeon is provided with an enlarged open area in which he can work on the ligament 192, and at the same time he has protected the median nerve 194 from the operating area. The surgeon has full visualization and working of the entire space, not a limited vision area as with other systems. This type of operation can, of course, be performed also with a mechanically expandable retractor not having a bladder thereon.

Indicated schematically at 193 in FIG. 20 is means for measuring the retractive force applied by the expanding portion of the retractor 160. This can be any suitable apparatus for measuring the force needed to bring together the grips 172 and 174, for example. With the retractor of FIGS. 1–5, a torque wrench or other instrument can be used to measure the force needed to turn the nut 16. Similarly, any known apparatus can be used to monitor the fluid pressure inside an expandable bladder on a retractor of the present invention. Thus, with any of the present retractors, the expansion force can be monitored and controlled.

FIGS. 24 and 25 illustrate another embodiment of the mechanically expandable retractors in accordance with the present invention. The retractor 210 illustrated in FIGS. 24 and 25 is a non-cannula type retractor. It does not have a central passage extending longitudinally through the retractor, but rather is solid or needle-like. Accordingly, the retractor 210 may be made slimmer if desired. It may be desirable to use such a non-canula type retractor in a situation where the surgeon is already employing a cannula through which instruments and/or a scope may be passed. The retractor may have a removable trocar also.

The retractor 210 may have a pointed distal end portion 212 for easier insertion through tissues. (Alternatively, the retractor may be utilized in conjunction with a removable trocar. The pointed distal end portion would be the distal tip of a removable trocar which would be removed after placement of the expanding portion of the retractor in the desired location.) The retractor 210 has an expanding portion 60 with a plurality of expanding arms 62. Grooves 66, 68, and 70 in the sleeve 14 define the arms 62 and provide weakened portions to allow for radial expansion of the arms 62. Rotation of the nut 16 relative to the threaded proximal end portion 22 of the retractor body 214, shortens the distance between the nut 16 and the distal end 212 of the retractor body. The sleeve 14 is compressed axially, and the arms 62 expand radially outwardly.

The expanding portion of the retractor 210 illustrated in FIGS. 24 and 25 is oriented in the opposite direction longitudinally from the expanding portion of the retractor shown in FIGS. 1–5. Thus, the maximum point of expansion is spaced from the distal end of the retractor 210. However, this configuration provides an annular end face 216 at the proximal end of the expanding portion 60. Thus, the retractor 210 is usable to pull back on tissue, or to hook tissue to move it proximally. The retractor shown in FIGS. 1–5 would in such use slide out because its expanding portion has a conical shape with an apex at its proximal end. This "reversed" design can be revised in practice to place the maximum point of expansion closer to or at the distal end of the retractor.

FIGS. 26 and 27 illustrate the use of a pair of retractors in accordance with the present invention to perform arthroscopic surgery on the acromion 220 in the shoulder. The humeral head 222 is spaced from the acromion 220, with the rotator cuff 224 and the bursa 226 therebetween. The bursa 226 normally fits tight up against the surface 228 of the acromion 220, but is shown spaced therefrom for clarity. Because the bursa 226 is normally tight up against the surface 228 of the acromion 220, it is difficult to operate on the surface 228 of the acromion 220.

To gain access to the surface 228, a pair of retractors 230 and 232 are used. The retractor 230 is inserted through an incision 234 in the back 236 of the shoulder. The retractor 230 has an expanding portion 238 located below the surface of the skin. The retractor 230 has a projecting portion 240 located above the surface of the skin. The retractor 230 has a passage 242 to allow the passage of surgical instruments therethrough.

The retractor 232 is inserted through an incision 242 in the side of the shoulder. An expanding portion 244 of the retractor 232 is located below the surface of the skin. A projecting portion 246 of the retractor 232 is located above or outside of the skin. The retractor 232 has a central passage 248 to allow the passage of an arthroscope therethrough.

The retractor 230 is inserted through the incision 234 until its expanding portion 238 engages the surface 228 of the acromion 220. The expanding portion 238 is irregularly configured so as to stay relatively flat against the acromion 220 and expand 180° away to push the bursa 226 away from the surface 228. The expanding portion 238 is then expanded. The bursa 226 and rotator cuff 224 are forced away from the surface 228, creating a working and visualization space 250 against the surface 228. Similarly, the retractor 232 is inserted through the incision 242 until its expanding portion 244 engages the surface 228. The expanding portion 244 is then expanded. The bursa 226 and the rotator cuff 224 are forced away from the surface 228, enlarging the working and visualization space 250.

An arthroscope is then inserted through the passage 248 in the retractor 232 until its distal end is located in the space 250. A shaver is then inserted through the passage 242 in the retractor 230, until its distal end is also in the working space 250. The surgeon thus has both the arthroscope tip and the shaver in a clear volume adjacent the surface to be worked upon. The surgeon can then remove an area of bone 252 from the acromion 220, without interference from the bursa 226 and the rotator cuff 224 which are normally tight up against the surface 228.

The surgeon can manipulate the projecting portion 240 of the retractor 230, and the projecting portion 246 of the retractor 232, to further move the tissues as desired. For example, the surgeon can pull proximally on the projecting portion 246 of the retractor 232 to pull the bursa 226 and rotator cuff 224 away from the surface 228. The surgeon can use the retractor 230 as a lever, moving the projecting portion 240 thereof upwardly as viewed in FIG. 27 to move the expanding portion 238 relatively downwardly to move the bursa 226 and the rotator cuff 224 away from the surface 228. Tissue is not significantly damaged by the retractor 230.

Upon completion of the operation, the expanding portion 238 of the retractor 230 is contracted or collapsed, and the retractor 230 is removed from the operating site. The expanding portion 244 of the retractor 232 is contracted or collapsed, and the retractor 232 is removed from the operating site. The bursa 226 and the rotator cuff 224 regain their original position against the acromion 220.

In accordance with a feature of the present invention, a retractor in accordance with the present invention need not have a round shape as shown in the drawings. Because there is no relative rotation between the retractor body and the retractor sleeve, neither must be round, and the body and sleeve need not have the same cross-sectional configuration. For example, the retractor may have an elliptical or oblong shape if two cannulas or passages are formed therein. The shape may be flattened if a slimmer profile is needed to pass between certain tissue layers. A square cross-section may be provided if desired. This ability to use any shape provides more leeway in configuring the expanding portion of the retractor, because the expanding portion does not have to have a round cross-sectional configuration.

In accordance with another feature of the present invention, a retractor can also function as two or more cannulas side-by-side. In those Figures which illustrate a cannula-type retractor having both a tool hole and a scope hole at the distal end, the tool hole and the scope hole are the ends of longitudinally co-extensive passages extending through the retractor body. These passages or lumens serve as two cannulas.

As an example of these two features, FIGS. 28 through 30 illustrate a mechanical retractor 260 with an elliptical cross-section and a dual-cannula configuration. The retractor 260 has a pair of passages 262 and 264 extending longitudinally through the retractor. The retractor 260 has an expanding portion 266 with a plurality of expanding arms 268. Grooves 270, 272, and 274 in the retractor sleeve 276 define the arms 268 and provide weakened portions to allow for radial expansion of the arms 268. When the sleeve 276 is compressed axially the arms 268 expand radially outwardly from the unexpanded condition shown in FIG. 19 to the expanded condition shown in FIG. 20.

In accordance with another feature of the present invention, the retractors incorporate a projecting portion at their proximal ends for manipulating the retractor. The projecting portion projects from the surface of the body tissues when the retractor is in use. In FIGS. 1–5, for example, the proximal end portion 22 of the retractor body 12 and the proximal end portion 42 of the sleeve 14, along with the nut 16, project from the surface of the body tissues when the retractor is in use. The retractor 10, when expanded, can thus be used to pull or push on tissue to move the tissue subcutaneously. Similarly, the retractor 160 illustrated in FIGS. 20 through 23 has parts projecting outwardly of the incision 190 to allow external manipulation of the sub-surface portion of the retractor.

This external projecting portion (or handle) is useful in many ways. It allows the surgeon to move tissues at will by pulling or pushing on the retractor or using it as a lever to move tissue subcutaneously. The surgeon can control the working point deep within the tissues because he can control the exposed portion of the retractor. Also, it allows the surgeon to block fluid flow, as an expanded retractor can be pulled back to seal flow and give more room to see and work. The retractor can also free up one hand for the surgeon.

These are all features which are available to a surgeon in open surgery, but not in arthroscopic surgery unless using a retractor as described herein. The intermediate portion of a retractor of the present invention is rigid enough to provide for such manipulation and to provide for precise positioning of the expandable portion within the body tissues. Alternatively, the intermediate portion can be flexible or selectively rigidifiable to provide some flexibility as desired in addition.

A retractor in accordance with the present invention is small and light weight, and thus can be packaged under sterile conditions and be disposable to maintain sterility. Current retractors have been constructed which are about 85 mm long, about 7 mm across in an unexpanded condition, and about 17 mm across when expanded. The amount of expansion can be greater or less. The dimensions will vary significantly, of course, with the particular surgical application. The number and placement of expanding portions or expanding arms will vary with the application also.

Retractors have been constructed of polymers such as nylon, but can be injection molded of other materials also. Retractors can also be constructed of polymers, composites, metal such as aluminum, etc. and can have one portion of one material and another portion of another dissimilar material. The surface of the material can be pebbled or roughened or ridged, or have serrated edges, to better grip tissue and hold the retractor in position. Of course, the surface must still remain smooth enough so as not to damage significantly the tissue it contacts. The expanding arms can be made of different materials from the remainder of the sleeve or of the retractor. A suitable material for the expandable bladder 130 is Silastic® elastomer, which is available from Dow Corning in medical grades.

The retractor also need not be straight as shown in the drawings. The retractor can be angled or bent, for example at a 45° or 90° angle, in the intermediate portion. Appropriate means for transmitting force at an angle are provided in such case in order to be able to shorten the sleeve to expand the arms.

The expandable portion 60 can be made of a biodegradable material, and can be made detachable from the remainder of the retractor. Similarly, the expandable bladder 130 can be made of a biodegradable material, and can be made detachable from the remainder of the retractor. In such a case, the biodegradable portion can be detached and left in the body after surgery. This is useful, for example, to prevent adjacent tissue planes from scarring together after surgery. The biodegradable mass will in time disappear, allowing the tissues to adjoin after they are healed.

The expandable portion 60 or the expandable bladder 130, or even the entire retractor, can be made of a transparent material to provide a better view of the operating area and improved visualization.

The amount of expansion of the retractors can be varied. Retractors of the present invention can be constructed which will expand up to 600% or more in transverse dimension. Retractors of the present invention can be constructed which will from about a few millimeters up to about several centimeters or more, as is desirable to operate in certain areas such as a knee or shoulder joint. This is unattainable by any other available device.

From the above description of the invention, those skilled in the art will perceive improvements, changes and modifications. Such improvements, changes and modifications within the skill of the art are intended to be covered by the appended claims.

I claim:

1. A retractor for forming a space at a location in body tissue which is free of naturally occurring space to facilitate arthroscopic surgery, said retractor comprising a body portion having a distal end portion, a proximal end portion, and an intermediate portion disposed between said proximal and distal end portions, and a tubular sleeve at least partially enclosing said body portion, said sleeve having a distal end portion adjacent to said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a plurality of arms, each of said arms including a distal portion which is connected with the distal end portion of said sleeve and a proximal portion which is connected with the intermediate portion of said sleeve, said distal and proximal portions of said arms being interconnected by connector portions of said arms, said connector portions of said arms having a first edge portion and a second edge portion which is opposite from said first edge portion, said arms being movable from a retracted condition to an extended condition by movement of said sleeve relative to said body portion and deflection of said arms at said connector portions of said arms to form open space which is asymmetrical relative to a central axis of said body portion at the location in the body tissue which is free of naturally occurring space, said connector portion of a first one of said arms being spaced from a connector portion of a second one of said arms by a first distance when said arms are in the extended condition, said second one of said arms being the arm which is next adjacent to the first edge portion of said connector portion of said first one of said arms, said connector portion of said first one of said arms being spaced from a connector portion of a third one of said arms by a second distance which is greater than said first distance when said arms are in the extended condition, said third one of said arms being the arm which is next adjacent to the second edge portion of said connector portion of said first one of said arms, said arms having means for forming the space which is asymmetrical relative to the central axis of said body portion by moving body tissue further away from the central axis of said body portion at a location between said first one of said arms and said second one of said arms than at a location between said first one of said arms and said third one of said arms upon movement of said arms from the retracted condition to the extended condition.

2. A retractor as set forth in claim 1 further including barrier means for blocking space at a location between at least some of said plurality of arms when said plurality of arms are in the extended condition, said barrier means being ineffective to block space between said first one of said arms and said third one of said arms.

3. A retractor as set forth in claim 1 wherein said sleeve includes a second plurality of arms disposed between said intermediate portion of said sleeve and said proximal end portion of said sleeve, said second plurality of arms being spaced apart in an axial direction along said body portion from said first plurality of arms, said second plurality of arms being deflectable from a retracted condition to an extended condition by movement of said sleeve relative to said body portion.

4. A retractor as set forth in claim 3 further including an elongated side opening formed in said sleeve and extending between said plurality of arms in said distal end portion of said sleeve and said second plurality of arms, said body portion including surface means for defining a passage which extends from said proximal end portion to said distal end portion of said body portion and which is adapted to receive an instrument during arthroscopic surgery, said body portion having an elongated side opening connecting said side opening in said sleeve with said passage in said body portion.

5. A retractor as set forth in claim 1 further including a side opening formed in said sleeve between said first one of said arms and said third one of said arms, said body portion including surface means for defining a passage which extends from said proximal end portion to said distal end portion of said body portion and which is adapted to receive an instrument during arthroscopic surgery, said body portion having a side opening connecting said side opening in said sleeve with said passage in said body portion.

6. A retractor as set forth in claim 1 wherein at least said connector portions of said arms are spaced apart from each other and from said body portion when said arms are in the extended condition, said retractor further including barrier means for blocking movement of tissue into space between at least some of said arms and said body portion when said arms are in the extended condition.

7. A retractor as set forth in claim 1 wherein said arms are formed of biodegradable material which degrades after prolonged exposure to tissue.

8. A retractor as set forth in claim 1 wherein said arms are formed of transparent material to facilitate viewing of tissue.

9. A retractor as set forth in claim 1 wherein said body portion and said sleeve are formed of transparent material to facilitate viewing of tissue.

10. A retractor as set forth in claim 1 wherein said retractor further includes barrier means formed of transparent material for blocking movement of tissue into space at a location between said connector portions of at least some of said arms and body portion when said arms are in the extended condition and for facilitating viewing of tissue.

11. A retractor as set forth in claim 10 wherein said arms are formed of transparent material to further facilitate viewing of tissue.

12. A retractor as set forth in claim 1 wherein said distal portions of said arms and said proximal portions of said arms form a construct having the same general configuration as a portion of a cone when said arms are in the extended condition, said distal portions of said arms forming the base of the cone, said proximal portions of said arms forming sloping side surface areas of the cone.

13. A retractor as set forth in claim 1 where the distal end of said sleeve has a circular configuration, said distal portions of said arms extending radially outwardly from said distal end of said sleeve when said arms are in the extended condition.

14. A cannula for forming a space in body tissue to facilitate arthroscopic surgery, said cannula comprising a body portion having a distal end portion, a proximal end portion, and an intermediate portion disposed between said proximal and distal end portions, said body portion including surface means for defining a passage which extends from said proximal end portion to said distal end portion of said body portion and which is adapted to receive an instrument during arthroscopic surgery, said passage in said body portion including surface means for defining a first elongated opening which extends axially along said body portion from the distal end portion of said body portion into the intermediate portion of said body portion and through which the instrument can move to engage body tissue during the performance of arthroscopic surgery, and a tubular sleeve at least partially enclosing said body portion, said sleeve having a distal end portion connected with said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a first plurality of arms, each of said arms of said first plurality of arms including a distal portion which is connected with a distal end of said sleeve and a proximal portion which is connected with the intermediate portion of said sleeve, said arms of said first plurality of arms being movable from a retracted condition to an extended condition by movement of said sleeve relative to said body portion and deflection of said arms of said first plurality of arms at locations between said distal portions of said arms of said first plurality of arms and said proximal portions of said arms of said first plurality of arms to at least partially form in the body tissue an open space into which the instrument can move from the first elongated opening during the performance of arthroscopic surgery, said intermediate portion of said sleeve including a second plurality of arms which are axially spaced along said sleeve from said first plurality of arms, each of said arms of said second plurality of arms including a distal portion which is connected with said intermediate portion of said sleeve at a location which is axially spaced from locations where said proximal portions of said first plurality of arms are connected with said intermediate portion of said sleeve, each of said arms of said second plurality of arms including a proximal portion which is connected with said proximal portion of said sleeve, said arms of said second plurality of arms being movable from a retracted condition to an extended condition by movement of said sleeve relative to said body portion and deflection of said arms of said second plurality of arms at locations between said distal portions of said arms of said second plurality of arms and said proximal portions of said arms of said second plurality of arms to at least partially form in the body tissue open space into which the instrument can move from the first elongated opening during the performance of arthroscopic surgery, said sleeve having an axially extending portion which is disposed between the proximal portions of the arms of said first plurality of arms and said distal portions of said arms of said second plurality of arms, said axially extending portion of said sleeve being disposed in engagement with said body portion when said arms of said first plurality of arms and said arms of said second plurality of arms are in their extended conditions, said first elongated opening in said body portion facing outward of said body portion in a direction transverse to a longitudinal central axis of said body portion, said first elongated opening in said body portion extending axially along said body portion from a location adjacent to a distal end of said body portion and the distal portions of said arms of said first plurality of arms at least to a location adjacent to ends of the proximal portions of said arms of said second plurality of arms where the proximal portions of said arms of said second plurality of arms are connected with said proximal portion of said sleeve when said arms of said first plurality of arms and said arms of said second plurality of arms are in their extended conditions, said sleeve including surface means for defining a second elongated opening which extends along said sleeve from a location adjacent to the distal end of said body portion and the distal portions of said arms of said first plurality of arms through said axially extending portion of said sleeve disposed between said first plurality of arms and said second plurality of arms to at least a location adjacent to the proximal portions of said arms of said second plurality of arms where the proximal portions of said arms of said second plurality of arms are connected with said proximal portion of said sleeve, said second elongated opening in said sleeve being aligned with said first elongated opening in said body portion and opening outward of said body portion in the direction transverse to the longitudinal central axis of said body portion when said arms of said first plurality of arms and said arms of said second plurality of arms are in their extended conditions to enable the instrument to move from the passage through the first elongated opening and into open space at least partially disposed between said body portion and portions of said first and second pluralities of arms when said first and second pluralities of arms are in their extended conditions.

15. A cannula as set forth in claim 14 wherein said distal portions of said arms of said first plurality of arms have a first length, said proximal portions of said arms of said first plurality of arms have a second length which is greater than said first length, said distal portions of said arms of said first plurality of arms extending generally perpendicular to the longitudinal central axis of said body portion at a first angle when said first plurality of arms are in the extended condition, said proximal portions of said arms of said first plurality of arms being skewed relative to the longitudinal central axis of said body portion at a second angle which is substantially smaller than said first angle when said first plurality of arms are in the extended condition.

16. A cannula as set forth in claim 14 wherein said second elongated opening in said sleeve is at least partially formed between a first one of said arms of said first plurality of arms and a second one of said arms of said first plurality of arms and is at least partially formed between a first one of said arms of said second plurality of arms and a second one of said arms of said second plurality of arms, said cannula further including barrier means which extends between at least some of said arms of said first plurality of arms and at least some of said arms of said second plurality of arms to block space at a location between arms of said first plurality of arms and at a location between arms of said second plurality of arms, said barrier means being ineffective to block the second elongated opening in said sleeve between the first one of said arms of said first plurality of arms and the second one of said arms of said first plurality of arms and between the first one of said arms of said second plurality of arms and the second one of said arms of said second plurality of arms to enable the instrument to move through the second elongated opening between the first one of said arms of said first plurality of arms and the second one of said arms of said first plurality of arms and to enable the instrument to move through the second elongated opening between the first one of said arms of said second plurality of arms and the second one of said arms of the second plurality of arms.

17. A cannula as set forth in claim 14 wherein said distal portions of said arms of said first plurality of arms have a first length, said proximal portions of said arms of said first plurality of arms have a second length which is greater than said first length, said distal portions of said arms of said first plurality of arms extending at a first angle to the longitudinal central axis of said body portion when said first plurality of arms are in the extended condition, said proximal portions of said arms of said first plurality of arms extending at a second angle to the longitudinal central axis of said body portion when said first plurality of arms are in the extended condition, said first angle being larger than said second angle, said distal portions of said arms of said second plurality of arms having a third length, said proximal portions of said arms of said second plurality of arms having a fourth length which is greater than said third length, said distal portions of said arms of said second plurality of arms extending at a third angle to the longitudinal central axis of said body portion when said second plurality of arms are in the extended condition, said proximal portions of said arms of said second plurality of arms extending at a fourth angle to the longitudinal central axis of said body portion when said second plurality of arms are in the extended condition, said third angle being larger than said fourth angle.

18. A cannula as set forth in claim 14 wherein said second elongated opening in said sleeve is at least partially formed between a first one of said arms of said first plurality of arms and a second one of said arms of said first plurality of arms, said cannula further including barrier means which extends between at least some of said arms of said first plurality of arms to block space between arms of said first plurality of arms, said barrier means being ineffective to block the second elongated opening in said sleeve at a location between the first one of said arms of said first plurality of arms and the second one of said arms of the first plurality of arms.

19. A cannula as set forth in claim 14 wherein said distal and proximal portions of said arms of said first plurality of arms are interconnected by connector portions of said arms of said first plurality of arms, said distal and proximal portions of said arms of said second plurality of arms being interconnected by connector portions of said arms of said second plurality of arms, said connector portion of a first one of said arms of said first plurality of arms being spaced from a connector portion of a second one of said arms of said first plurality of arms by a first distance when said arms of said first plurality of arms are in the extended condition, said second one of said arms of said first plurality of arms being the arm of said first plurality of arms which is next adjacent to a first edge portion of said first one of said arms of said first plurality of arms, said connector portion of said first one of said arms of said first plurality of arms being spaced from a connector portion of a third one of said arms of said first plurality of arms by a second distance which is greater than said first distance, said third one of said arms of said first plurality of arms being the arm of said first plurality of arms which is next adjacent to a second edge portion of said first one of said arms of said first plurality of arms, said second elongated opening being at least partially disposed between the second edge portion of said first one of said arms of said first plurality of arms and a first edge portion of said third one of said arms of said first plurality of arms, said connector portion of a first one of said arms of said second plurality of arms being spaced from a connector portion of a second one of said arms of said second plurality of arms by a third distance when said arms of said second plurality of arms are in the extended condition, said second one of said arms of said second plurality of arms being the arm of said second plurality of arms which is next adjacent to a first edge portion of said first one of said arms of said second plurality of arms, said connector portion of said first one of said arms of said second plurality of arms being spaced from a connector portion of a third one of said arms of said second plurality of arms by a fourth distance which is greater than said third distance, said third one of said arms of said second plurality of arms being the arm of said second plurality of arms which is next adjacent to a second edge portion of said first one of said arms of said second plurality of arms, said second elongated opening being at least partially disposed between the second edge portion of said first one of said arms of said second plurality of arms and a first edge portion of a third one of said arms of said second plurality of arms.

20. A cannula for forming a space at a location in body tissue which is free of naturally occurring space to facilitate arthroscopic surgery, said cannula comprising a body portion having a distal end portion, a proximal end portion, and an intermediate portion disposed between said proximal and distal end portions, said body portion including surface means for defining a passage which extends from said proximal end portion to said distal end portion of said body portion and which is adapted to receive an instrument during arthroscopic surgery, said passage in said body portion including surface means for defining an opening in the distal end portion of said body portion and through which the instrument can move to engage body tissue at the location in the body tissue which is free of naturally occurring space during the performance of arthroscopic surgery, and a tubular sleeve at least partially enclosing said body portion, said sleeve having a distal end portion connected with said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a plurality of arms, each of said arms including a distal portion which is connected with a distal end of said sleeve and a proximal portion which is connected with the intermediate portion of said sleeve, said distal portions of said arms having a first length, said proximal portions of said arms having a second length which is greater than said first length, said arms being movable from a retracted condition to an extended condition by movement of said sleeve relative to said body portion and deflection of said arms at locations between said distal portions of said arms and said proximal portions of said arms to said form space at the location in the body tissue which is free of naturally occurring space and into which the instrument can move from the passage opening during the performance of arthroscopic surgery, said distal portions of said arms extending transversely to a longitudinal central axis of said sleeve at a first angle when said arms are in the extended condition, said proximal portions of said arms extending relative to the central axis of said sleeve at a second angle which is substantially smaller than said first angle when said arms are in the extended condition, said proximal portions of said arms having means for forming an open space in the body tissue by moving body tissue away from said distal portions of said arms and away from a distal end of said body portion upon movement of said arms from the retracted condition to the extended condition to form an open space in the body tissue adjacent to the distal end of said body portion to facilitate the performance of arthroscopic surgery on the body tissue at the location which is free of naturally occurring space, said passage opening being in communication with the open space formed in the body tissue by movement of body tissue by said outer proximal portions of said arms during movement of said arms from the retracted condition to the extended condition to enable the instrument to move through said passage opening into the open space at the location in the body tissue which is free of naturally occurring space, said distal and proximal portions of said arms being interconnected by connector portions of said arms, said connector portion of a first one of said arms being spaced from said connector portion of a second one of said arms by a first distance when said arms are in the extended condition, said second one of said arms being the arm which is next adjacent to a first edge portion of said first one of said arms, said connector portion of said first one of said arms being spaced from said connector portion of a third one of said arms by a second distance which is greater than said first distance when said arms are in the extended condition, said third one of said arms being the arm which is next adjacent to a second edge portion of said first one of said arms.

21. A cannula as set forth in claim 20 wherein said connector portion of a fourth one of said arms is spaced from said connector portion of said third one of said arms by said first distance when said arms are in the extended condition, said fourth one of said arms being the arm which is next adjacent to a first edge portion of said third one of said arms.

22. A cannula as set forth in claim 20 further including barrier means for blocking space between said first edge portion of said first one of said arms and said second arm and for blocking space between said second and third arms when said arms are in the extended condition, said barrier means being ineffective to block space at a location between said second edge portion of said first one of said arms and said third arm when said arms are in the extended condition.

23. A cannula as set forth in claim 20 wherein said surface for defining an elongated opening in said body portion and which faces outward of said body portion in a direction transverse to a longitudinal central axis of said body portion and toward a location between said second edge portion of said first one of said arms and said third one of said arms and which extends axially along said body portion from a location adjacent to the distal end of said body portion and the distal portions of said arms at least to a location adjacent to ends of the proximal portions of said first one of said arms and said third one of said arms where the proximal portions of said first one of said arms and said third one of said arms are connected with said intermediate portion of said sleeve when said arms are in the extended condition to enable the instrument to move from the passage through the elongated opening in said body portion.

24. A cannula for forming a space at a location in body tissue which is free of naturally occurring space to facilitate arthroscopic surgery, said cannula comprising a body portion having a distal end portion, a proximal end portion, and an intermediate portion disposed between said proximal and distal end portions, said body portion including surface means for defining a passage which extends from said proximal end portion to said distal end portion of said body portion and which is adapted to receive an instrument during arthroscopic surgery, said passage in said body portion including surface means for defining an opening in the distal end portion of said body portion and through which the instrument can move to engage body tissue at the location in the body tissue which is free of naturally occurring space during the performance of arthroscopic surgery, and a tubular sleeve at least partially enclosing said body portion, said sleeve having a distal end portion connected with said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a plurality of arms, each of said arms including a distal portion which is connected with a distal end of said sleeve and a proximal portion which is connected with the intermediate portion of said sleeve, said distal portions of said arms having a first length, said proximal portions of said arms having a second length which is greater than said first length, said arms being movable from a retracted condition to an extended condition by movement of said sleeve relative to said body portion and deflection of said arms at locations between said distal portions of said arms and said proximal portions of said arms to form space at the location in the body tissue which is free of naturally occurring space and into which the instrument can move from the passage opening during the performance of arthroscopic surgery, said distal portions of said arms extending generally perpendicular to a longitudinal central axis of said sleeve at a first angle when said arms are in the extended condition, said proximal portions of said arms being skewed relative to the central axis of said sleeve at a second angle which is substantially smaller than said first angle when said arms are in the extended condition, said proximal portions of said arms having means for forming an open space in the body tissue at the location which is free of naturally occurring space by moving body tissue away from said distal portions of said arms and away from a distal end of said body portion upon movement of said arms from the retracted condition to the extended condition to form an open space in the body tissue adjacent to the distal end of said body portion to facilitate the performance of arthroscopic surgery on the body tissue at the location which is free of naturally occurring space, said passage opening being in communication with the open space formed in the body tissue by movement of body tissue by said proximal portions of said arms during movement of said arms from the retracted condition to the expanded condition to enable the instrument to move through said passage opening into the open space at the location in the body tissue which is free of naturally occurring space, said body portion and said sleeve have a cylindrical configuration when said arms are in the retracted condition, said passage opening extends axially along said body portion from a location adjacent to the distal end of said body portion and the distal portions of said arms at least to a location adjacent to the proximal portions of said arms to enable the instrument to move from the passage through the opening, said opening facing radially outward of said body portion, said sleeve including surface means for at least partially defining a slot which extends axially along said sleeve from a location adjacent to the distal end of said body portion and the distal portions of said arms at least to a location adjacent to the proximal portions of said arms, said slot in said sleeve being radially aligned with said opening in said body portion to enable the instrument to move from the passage through the opening in said body portion and into space at least partially disposed between said body portion and said proximal portions of said arms and formed in the body tissue at the location which is free of naturally occurring space by movement of body tissue by said proximal portions of said arms upon movement of said arms from the retracted condition to the extended condition, said distal and proximal portions of said arms being interconnected by connector portions of said arms, said connector portions of said arms having a first edge portion and a second edge portion which is opposite from said first edge portion, said connector portion of a first one of said arms being spaced from a connector portion of a second one of said arms by a first distance when said arms are in the extended condition, said second one of said arms being the arm which is next adjacent to the first edge portion of said connector portion of said first one of said arms, said connector portion of said first one of said arms being spaced from a connector portion of a third one of said arms by a second distance which is greater than said first distance when said arms are in the extended condition, said third one of said arms being the arm which is next adjacent to the second edge portion of said connector portion of said first one of said arms, said opening in said body portion and said slot in said sleeve opening radially outward toward space between proximal portions of said first one of said arms and said third one of said arms when said arms are in the extended condition.

25. A cannula as set forth in claim 24 further including barrier means for blocking space between at least some of the arms of said plurality of arms when said plurality of arms are in the extended condition, said barrier means being ineffective to block space at a location between said first one of said arms and said third one of said arms to enable the instrument to move between said first one of said arms and said third one of said arms, said barrier means being effective to block movement of the instrument between arms other than said first one of said arms and said third one of said arms.

26. A cannula as set forth in claim 24 wherein said distal portions of said arms and said proximal portions of said arms form a construct having the same general configuration as a portion of a cone when said arms are in the extended condition, said distal portions of said arms forming the base of the cone, said outer side surface means of said proximal portions of said arms forming sloping side surface areas of the cone, said sloping side surface areas of the cone being effective to apply force against the body tissue to maintain the open space in the body tissue at the location which is free of naturally occurring space during the performance of arthroscopic surgery.

27. A cannula as set forth in claim 26 further including first areas of reduced thickness connecting ends of said proximal portions of said arms with said intermediate portion of said sleeve, second areas of reduced thickness connecting ends of said distal portions of said arms with the distal end of said sleeve, and third areas of reduced thickness connecting said distal portions of said arms with said proximal portions of said arms.

28. A cannula as set forth in claim 26 where a distal end of said sleeve has a circular configuration, said distal portions of said arms extending radially outwardly from said distal end of said sleeve when said arms are in the extended condition.

29. A cannula for forming a space at a location in body tissue which is free of naturally occurring space to facilitate arthroscopic surgery, said cannula comprising a body portion having a distal end portion, a proximal end portion, and an intermediate portion disposed between said proximal and distal end portions, said body portion including surface means for defining a passage which extends from said proximal end portion to said distal end portion of said body portion and which is adapted to receive an instrument during arthroscopic surgery, said passage in said body portion including surface means for defining an opening in the distal end portion of said body portion and through which the instrument can move to engage body tissue at the location in the body tissue which is free of naturally occurring space during the performance of arthroscopic surgery, and a tubular sleeve at least partially enclosing said body portion, said sleeve having a distal end portion connected with said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a plurality of arms, each of said arms including a distal portion which is connected with a distal end of said sleeve and a proximal portion which is connected with the intermediate portion of said sleeve, said distal portions of said arms having a first length, said proximal portions of said arms having a second length which is greater than said first length, said arms being movable from a retracted condition to an extended condition by movement of said sleeve relative to said body portion and deflection of said arms at locations between said distal portions of said arms and said proximal portions of said arms to form space at the location in the body tissue which is free of naturally occurring space and into which the instrument can move from the passage opening during the performance of arthroscopic surgery, said distal portions of said arms extending generally perpendicular to a longitudinal central axis of said sleeve at a first angle when said arms are in the extended condition, said proximal portions of said arms being skewed relative to the central axis of said sleeve at a second angle which is substantially smaller than said first angle when said arms are in the extended condition, said proximal portions of said arms having means for forming an open space in the body tissue at the location which is free of naturally occurring space by moving body tissue away from said distal portions of said arms and away from a distal end of said body portion upon movement of said arms from the retracted condition to the extended condition to form an open space in the body tissue adjacent to the distal end of said body portion to facilitate the performance of arthroscopic surgery on the body tissue at the location which is free of naturally occurring space, said passage opening being in communication with the open space formed in the body tissue by movement of body tissue by said proximal portions of said arms during movement of said arms from the retracted condition to the expanded condition to enable the instrument to move through said passage opening into the open space at the location in the body tissue which is free of naturally occurring space, said distal portions of said arms being spaced apart and disposed in a circular array with different spacings between adjacent distal portions of at least some of said arms when said arms are in the extended condition.

30. A cannula as set forth in claim 29 further including a side opening formed in said distal end portion of said sleeve between said plurality of arms in said distal end portion of said sleeve, said opening in the distal end portion of said body portion connecting said side opening in said sleeve in communication with said passage in said body portion.

31. A cannula as set forth in claim 29 further including barrier means for blocking movement of tissue into space between said arms and said body portion when said arms are in the extended condition.

32. A cannula as set forth in claim 29 further including barrier means formed of transparent material for blocking movement of tissue into space at a location between said arms and body portion when said arms are in the extended condition and for facilitating viewing of tissue.

33. A cannula as set forth in claim 32 wherein said arms are formed of transparent material to further facilitate viewing of tissue.

34. A cannula as set forth in claim 29 wherein said body portion and said sleeve have a cylindrical configuration when said arms are in the retracted condition, said passage opening extends axially along said body portion from a location adjacent to the distal end of said body portion and the distal portions of said arms at least to a location adjacent to the proximal portions of said arms to enable the instrument to move from the passage through the groove, said opening facing radially outward of said body portion, said sleeve including surface means for at least partially defining a slot which extends axially along said sleeve from a location adjacent to the distal end of said body portion and the distal portions of said arms at least to a location adjacent to the proximal portions of said arms, said slot in said sleeve being radially aligned with said opening in said body portion to enable the instrument to move from the passage through the opening in said body portion and into space at least partially disposed between said body portion and said proximal portions of said arms and formed in the body tissue at the location which is free of naturally occurring space by movement of body tissue by said proximal portions of said arms upon movement of said arms from the retracted condition to the extended condition.

35. A cannula as set forth in claim 25 wherein said sleeve includes a second plurality of arms disposed between said intermediate portion of said sleeve and said proximal end portion of said sleeve, said second plurality of arms being deflectable from a retracted condition to an extended condition by movement of said sleeve relative to said body portion to form space which extends between said second plurality of arms and the distal end portion of said sleeve at the location in the body tissue which is free of naturally occurring space.

36. A cannula as set forth in claim 29 wherein said arms are formed of biodegradable material which degrades after prolonged exposure to tissue.

37. A cannula as set forth in claim 29 wherein said arms are formed of transparent material to facilitate viewing of tissue.

38. A cannula as set forth in claim 29 wherein said body portion and said sleeve are formed of transparent material to facilitate viewing of tissue.

39. A cannula for forming a space at a location in body tissue which is free of naturally occurring space to facilitate arthroscopic surgery, said cannula comprising a body portion having a distal end portion, a proximal end portion, and an intermediate portion disposed between said proximal and distal end portions, said body portion including surface means for defining a passage which extends from said proximal end portion to said distal end portion of said body portion and which is adapted to receive an instrument during arthroscopic surgery, said passage in said body portion including surface means for defining an opening in the distal end portion of said body portion and through which the instrument can move to engage body tissue at the location in the body tissue which is free of naturally occurring space during the performance of arthroscopic surgery, and a tubular sleeve at least partially enclosing said body portion, said sleeve having a distal end portion connected with said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a plurality of arms, each of said arms including a distal portion which is connected with a distal end of said sleeve and a proximal portion which is connected with the intermediate portion of said sleeve, said distal portions of said arms having a first length, said proximal portions of said arms having a second length which is greater than said first length, said arms being movable from a retracted condition to an extended condition by movement of said sleeve relative to said body portion and deflection of said arms at locations between said distal portions of said arms and said proximal portions of said arms to form space at the location in the body tissue which is free of naturally occurring space and into which the instrument can move from the passage opening during the performance of arthroscopic surgery, said distal portions of said arms extending generally perpendicular to a longitudinal central axis of said sleeve at a first angle when said arms are in the extended condition, said proximal portions of said arms being skewed relative to the central axis of said sleeve at a second angle which is substantially smaller than said first angle when said arms are in the extended condition, said proximal portions of said arms having means for forming an open space in the body tissue at the location which is free of naturally occurring space by moving body tissue away from said distal portions of said arms and away from a distal end of said body portion upon movement of said arms from the retracted condition to the extended condition to form an open space in the body tissue adjacent to the distal end of said body portion to facilitate the performance of arthroscopic surgery on the body tissue at the location which is free of naturally occurring space, said passage opening being in communication with the open space formed in the body tissue by movement of body tissue by said proximal portions of said arms during movement of said arms from the retracted condition to the expanded condition to enable the instrument to move through said passage opening into the open space at the location in the body tissue which is free of naturally occurring space, said distal and proximal portions of said arms being interconnected by connector portions of said arms, said connector portion of a first one of said arms being spaced from a connector portion of a second one of said arms by a first distance when said arms are in the extended condition, said second one of said arms being the arm which is next adjacent to a first edge portion of said first one of said arms, said connector portion of said first one of said arms being spaced from a connector portion of a third one of said arms by a second distance which is greater than said first distance when said arms are in the extended condition, said third one of said arms being the arm which is next adjacent to a second edge portion of said first one of said arms.

40. A cannula as set forth in claim 39 wherein said body portion and said sleeve have a cylindrical configuration when said arms are in the retracted condition, said passage opening extends axially along said body portion from a location adjacent to the distal end of said body portion and the distal portions of said arms at least to a location adjacent to the proximal portions of said arms to enable the instrument to move from the passage through the groove, said opening facing radially outward of said body portion, said sleeve including surface means for at least partially defining a slot which extends axially along said sleeve from a location adjacent to the distal end of said body portion and the distal portions of said arms at least to a location adjacent to the proximal portions of said arms, said slot in said sleeve being radially aligned with said opening in said body portion to enable the instrument to move from the passage through the opening in said body portion and into space at least partially disposed between said body portion and said proximal portions of said arms and formed in the body tissue at the location which is free of naturally occurring space by movement of body tissue by said proximal portions of said arms upon movement of said arms from the retracted condition to the extended condition.

41. A cannula as set forth in claim 39 further including barrier means for blocking space between at least some of the arms of said plurality of arms when said plurality of arms are in the extended condition, said barrier means being ineffective to block space at a location between said first one of said arms and said third one of said arms to enable the instrument to move between said first one of said arms and said third one of said arms, said barrier means being effective to block movement of the instrument between arms other than said first one of said arms and said third one of said arms.

42. A cannula as set forth in claim 39 wherein said sleeve includes a second plurality of arms disposed between said intermediate portion of said sleeve and said proximal end portion of said sleeve, said second plurality of arms being deflectable from a retracted condition to an extended condition by movement of said sleeve relative to said body portion to form space which extends between said second plurality of arms and the distal end portion of said sleeve at the location in the body tissue which is free of naturally occurring space.

43. A cannula as set forth in claim 42 further including surface means for defining a side opening in said intermediate portion of said sleeve between said plurality of arms in said distal end portion of said sleeve and said second plurality of arms, said opening in the distal end portion of said body portion connecting said side opening in said sleeve with said passage in said body portion.

44. A cannula as set forth in claim 39 further including a side opening formed in said distal end portion of said sleeve between said plurality of arms-in said distal end portion of said sleeve, said opening in the distal end portion of said body portion connecting said side opening in said sleeve in communication with said passage in said body portion.

45. A cannula as set forth in claim 39 further including barrier means for blocking movement of tissue into space between said arms and said body portion when said arms are in the extended condition.

46. A cannula as set forth in claim 39 wherein said arms are formed of biodegradable material which degrades after prolonged exposure to tissue.

47. A cannula as set forth in claim 39 wherein said arms are formed of transparent material to facilitate viewing of tissue.

48. A cannula as set forth in claim 39 wherein said body portion and said sleeve are formed of transparent material to facilitate viewing of tissue.

49. A cannula as set forth in claim 39 further including barrier means formed of transparent material for blocking movement of tissue into space at a location between said arms and body portion when said arms are in the extended condition and for facilitating viewing of tissue.

50. A cannula as set forth in claim 49 wherein said arms are formed of transparent material to further facilitate viewing of tissue.

51. A cannula for forming a space at a location in body tissue which is free of naturally occurring space to facilitate arthroscopic surgery, said cannula comprising a body portion having a distal end portion, a proximal end portion, and an intermediate portion disposed between said proximal and distal end portions, said body portion including surface means for defining a passage which extends from said proximal end portion to said distal end portion of said body portion and which is adapted to receive an instrument during arthroscopic surgery, said passage in said body portion including surface means for defining an opening in the distal end portion of said body portion and through which the instrument can move to engage body tissue at the location in the body tissue which is free of naturally occurring space during the performance of arthroscopic surgery, and a tubular sleeve at least partially enclosing said body portion, said sleeve having a distal end portion connected with said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a plurality of arms, each of said arms including a distal portion which is connected with a distal end of said sleeve and a proximal portion which is connected with the intermediate portion of said sleeve, said distal portions of said arms having a first length, said proximal portions of said arms having a second length which is greater than said first length, said arms being movable from a retracted condition to an extended condition by movement of said sleeve relative to said body portion and deflection of said arms at locations between said distal portions of said arms and said proximal portions of said arms to form space at the location in the body tissue which is free of naturally occurring space and into which the instrument can move from the passage opening during the performance of arthroscopic surgery, said distal portions of said arms extending generally perpendicular to a longitudinal central axis of said sleeve at a first angle when said arms are in the extended condition, said proximal portions of said arms being skewed relative to the central axis of said sleeve at a second angle which is substantially smaller than said first angle when said arms are in the extended condition, said proximal portions of said arms having means for forming an open space in the body tissue at the location which is free of naturally occurring space by moving body tissue away from said distal portions of said arms and away from a distal end of said body portion upon movement of said arms from the retracted condition to the extended condition to form an open space in the body tissue adjacent to the distal end of said body portion to facilitate the performance of arthroscopic surgery on the body tissue at the location which is free of naturally occurring space, said passage opening being in communication with the open space formed in the body tissue by movement of body tissue by said proximal portions of said arms during movement of said arms from the retracted condition to the expanded condition to enable the instrument to move through said passage opening into the open space at the location in the body tissue which is free of naturally occurring space, said sleeve includes a second plurality of arms disposed between said intermediate portion of said sleeve and said proximal end portion of said sleeve, said second plurality of arms being deflectable from a retracted condition to an extended condition by movement of said sleeve relative to said body portion to form space which extends between said second plurality of arms and the distal end portion of said sleeve at the location in the body tissue which is free of naturally occurring space, surface means for defining a side opening in said intermediate portion of said sleeve between said plurality of arms in said distal end portion of said sleeve and said second plurality of arms, said opening in the distal end portion of said body portion connecting said side opening in said sleeve with said passage in said body portion.

52. A cannula as set forth in claim 517 wherein said arms of said second plurality of arms are spaced apart and disposed in a circular array with different spacings between adjacent portions of at least some of said arms of said second plurality of arms when said arms of said second plurality of arms are in the extended condition.

53. A cannula for forming a space at a location in body tissue which is free of naturally occurring space to facilitate arthroscopic surgery, said cannula comprising a longitudinally extending body portion having a distal end portion, a proximal end portion, and an intermediate portion disposed between said proximal and distal end portions, said body portion including surface means for defining a passage which extends from said proximal end portion to said distal end portion of said body portion and which is adapted to receive an instrument during arthroscopic surgery, and a tubular sleeve at least partially enclosing said body portion, said sleeve having a distal end portion connected with said distal end portion of said body portion, said sleeve having a proximal end portion disposed adjacent to said proximal end portion of said body portion, said sleeve having an intermediate portion disposed between said distal and proximal end portions of said sleeve, said distal end portion of said sleeve including a plurality of arms, each of said arms including a distal portion which is connected with a distal end of said sleeve and a proximal portion which is connected with the intermediate portion of said sleeve, said arms being movable from a retracted condition to an extended condition by movement of said sleeve relative to said body portion and deflection of said arms at locations between said distal portions of said arms and said proximal portions of said arms to form space at the location in the body tissue which is free of naturally occurring space, said arms having means for forming an open space in the body tissue at the location which is free of naturally occurring space by moving body tissue away from said body portion upon movement of said arms from the retracted condition to the extended condition to form an open space in the body tissue to facilitate the performance of arthroscopic surgery on the body tissue at the location which is free of naturally occurring space, said surface means for defining a passage in said body portion including surface means for defining an elongated opening in said body portion and which faces outward of said body portion in a direction transverse to a longitudinal central axis of said body portion and which extends axially along said body portion from a location adjacent to a distal end of said body portion and the distal portions of said arms at least to a location adjacent to ends of the proximal portions of said arms where the proximal portions of said arms are connected with said intermediate portion of said sleeve when said arms are in the extended condition to enable the instrument to move from the passage through the elongated opening in said body portion, said sleeve including surface means for defining an elongated opening which extends axially along said sleeve from a location adjacent to the distal end of said body portion and the distal portions of said arms at least to a location adjacent to the proximal portions of said arms where the proximal portions of said arms are connected with said intermediate portion of said sleeve, said elongated opening in said sleeve being aligned with said elongated opening in said body portion and opens outward of said body portion in the direction transverse to the longitudinal central axis of said body portion when said arms are in the extended condition to enable the instrument to move from the passage through the elongated opening in said body portion and into open space at least partially disposed between said body portion and said proximal portions of said arms and formed in the body tissue at the location which is free of naturally occurring space by movement of body tissue by said arms upon movement of said arms from the retracted condition to the extended condition to enable the instrument to move through the passage and through the elongated opening in said body portion into the open space at the location in the body tissue which is free of naturally occurring space, said distal portions of said arms being spaced apart and disposed in a circular array with different spacings between adjacent distal portions of at least some of said arms when said arms are in the expanded condition.

54. A cannula as set forth in claim 53 wherein said elongated opening in said sleeve being formed between a first one of said arms and a second one of said arms, said cannula further including barrier means which extends between at least some of said arms to block space between said arms, said barrier means being ineffective to block the elongated opening at a location between the first one of said arms and the second one of said arms to enable the instrument to move through the elongated opening between the first one of said arms and the second one of said arms.

55. A cannula as set forth in claim 53 wherein said body portion includes surface means for defining an opening in the distal end of said body portion, said opening in the distal end of said body portion being connected in communication with said passage to enable an instrument to move through said passage to the opening in the distal end of said body portion.

56. A cannula as set forth in claim 53 wherein said elongated opening in said body portion extends past the location where the proximal portions of said arms are connected with said intermediate portion of said sleeve when said arms are in the extended condition.

57. A cannula as set forth in claim 53 wherein said distal portions of said arms have a first length, said proximal portions of said arms having a second length which is greater than said first length, said distal portions of said arms extending at a first angle to the longitudinal central axis of said body portion, said proximal portions of said arms extending at a second angle to the longitudinal central axis of said body portion, said second angle being less than said first angle.

58. A cannula as set forth in claim 53 wherein said distal portions of said arms have a first length and said proximal portions of said arms having a second length which is greater than said first length, said distal portions of said arms extending generally perpendicular to a longitudinal central axis of said sleeve at a first angle when said arms are in the extended condition, said proximal portions of said arms being skewed relative to the central axis of said sleeve at a second angle which is substantially smaller than said first angle when said arms are in the extended condition, said proximal portions of said arms having outer side surface means for transmitting force to move tissue away from said distal portions of said arms and the distal end of said body portion upon movement of said arms from the retracted condition to the extended condition.

59. A cannula as set forth in claim 53 wherein said distal portions of said arms and said proximal portions of said arms form a construct having the same general configuration as a portion of a cone when said arms are in the extended condition, said distal portions of said arms forming the base of the cone, said outer side surface means of said proximal portions of said arms forming sloping side surface areas of the cone.

60. A cannula as set forth in claim 53 further including first areas of reduced thickness connecting ends of said proximal portions of said arms with said intermediate portion of said sleeve, second areas of reduced thickness connecting ends of said distal portions of said arms with the distal end of said sleeve, and third areas of reduced thickness connecting said distal portions of said arms with said proximal portions of said allils.

61. A cannula as set forth in claim 53 wherein the distal end of said sleeve has a circular configuration, said distal portions of said arms extending radially outward from said distal end of said sleeve when said arms are in the extended condition.

62. A cannula as set forth in claim 53 wherein said distal and proximal portions of said arms are interconnected by connector portions of said arms, said connector portion of said first arm being spaced from a connector portion of said second arm by a first distance when said arms are in the extended condition, said connector portion of said first arm being spaced from a connector portion of a third one of said arms by a second distance which is less than said first distance when said arms are in the extended condition, said elongated opening in said sleeve being disposed between said first arm and said second arm.

63. A cannula as set forth in claim 53 wherein said sleeve includes a second plurality of arms disposed between said intermediate portion of said sleeve and said proximal end portion of said sleeve, said second plurality of arms being deflectable from a retracted condition to an extended condition by movement of said sleeve relative to said body portion.

64. A retractor as set forth in claim 63 wherein said elongated opening formed in said sleeve is at least partially disposed between arms of said second plurality of arms.

65. A retractor as set forth in claim 53 wherein at least portions of said arms are spaced apart from each other and from said body portion when said arms are in the extended condition, said retractor further including barrier means for blocking movement of tissue into space at a location between at least some of said arms and said body portion when said arms are in the extended condition.

66. A retractor as set forth in claim 53 wherein said arms are formed of biodegradable material which degrades after prolonged exposure to tissue.

67. A retractor as set forth in claim 53 wherein said arms are formed of transparent material to facilitate viewing of tissue.

68. A retractor as set forth in claim 53 wherein said body portion and said sleeve are formed of transparent material to facilitate viewing of tissue.

69. A retractor as set forth in claim 53 wherein at least portions of some of said arms are spaced apart from each other and from said body portion when said arms are in the extended condition, said retractor further including barrier means formed of transparent material for blocking movement of tissue into space at a location between at least some of said arms and body portion when said arms are in the extended condition and for facilitating viewing of tissue.

70. A retractor as set forth in claim 53 wherein said arms are formed of transparent material to further facilitate viewing of tissue.

* * * * *